US006841358B1

(12) United States Patent
Locht et al.

(10) Patent No.: US 6,841,358 B1
(45) Date of Patent: Jan. 11, 2005

(54) **RECOMBINANT PROTEINS OF FILAMENTOUS HAEMAGGLUTININ OF BORDETELLA, PARTICULARLY *BORDETELLA PERTUSSIS*, METHOD FOR PRODUCING SAME, AND USES THEREOF FOR PRODUCING FOREIGN PROTEINS OF VACCINATING ACTIVE PRINCIPLES**

(75) Inventors: Camille Locht, Wannehain (FR); Genevieve Renauld, Lyons (FR); Andre Capron, Phalempin (FR); Gilles Riveau, Phalempin (FR); Franco Menozzi, Hyon (BE); Francoise Jacob-Dubuisson, Faches-Thumesnil (FR)

(73) Assignee: Institut Pasteur De Lille, Lille Cedex (FR)

( * ) Notice: Subject to any disclaimer, the term of this patent is extended or adjusted under 35 U.S.C. 154(b) by 0 days.

(21) Appl. No.: 08/765,287

(22) PCT Filed: Apr. 19, 1995

(86) PCT No.: PCT/FR95/00512

§ 371 (c)(1),
(2), (4) Date: Sep. 12, 1997

(87) PCT Pub. No.: WO95/28486

PCT Pub. Date: Oct. 26, 1995

(30) Foreign Application Priority Data

Apr. 19, 1994 (FR) .............................................. 94 04661

(51) Int. Cl.$^7$ ........................ C12N 15/09; C12P 21/06; A61K 39/00; A61K 39/02; A01N 63/00
(52) U.S. Cl. .................... 435/69.1; 435/69.3; 424/93.4; 424/184.1; 424/190.1
(58) Field of Search .............................. 435/69.1, 69.3, 435/71.1, 172.1, 172.2, 172.3; 424/184.1, 190.1, 93.4, 200.1, 234.1, 253.1

(56) References Cited

U.S. PATENT DOCUMENTS 6,036,960 A * 3/2000 Relman et al. .......... 424/253.1

FOREIGN PATENT DOCUMENTS

| EP | 0 453 216 A3 | 10/1991 |
| EP | 453216 | * 10/1991 |
| WO | 9004641 | * 5/1990 |

OTHER PUBLICATIONS

Menozzi et al. FEMS Microbiology Letters 78:59–64, 1991.*
Locht et al. Molecular Microbiology 9(4):653–660, 1993.*
Menozzi et al. Infection and Immunity 62(3): 769–778, 1994.*
Delisse–Gathoye et al. Infection and Immunity 58(9):2895–2905, 1990.*
Guzman et al. Microbial Pathogenesis 12:383–389, 1992.*
Miller, Jeff F., et al, *Journal of Bacteriology*, vol. 171, No. 11, 1989, pp. 6345–6348 "Analysis of *Bordetella pertussis* Virulence Gene Regulation by Use of Transcriptional Fusions in *Escherichia coli*".
Miller, Jeff F., et al, *Journal of Bacteriology*, vol. 174, No. 3, 1992, pp. 970–979, "Constitutive Sensory Transduction Mutations in the *Bordetella pertussis* bvgS Gene".
Roy, Craig R., et al, *Journal of Bacteriology*, vol. 173, No.7, 1991, pp. 2385–2392, "Identification of *Bordetella pertussis* Regulatory Sequences Required for Transcriptional Activation of the fhaB Gene and Autoregulation of the bvgAS Operon".
Delisse–Gathoye, Anne–Marie, et al, *Infection and Immunity*, vol. 58, No. 9, 1990, pp. 2895–2905, "Cloning, Partial Sequence, Expression, and Antigenic Analysis of the Filamentous Hemagglutinin Gene of Bordetella pertussis".
Menozzi, Franco D., et al, *Infection and Immunity*, vol. 62, No. 3, Mar. 1994, pp. 769–778, "Heparin–Inhibitable Lectin Activity of the Filamentous Hemagglutinin Adhesin of *Bordetella pertussis*".
Willems, Rob J.L., et al, *Molecular Microbiology*, vol. 11, No. 2, Jan. 1994, pp. 337–347, "Mutational analysis of the *Bordetella pertussis*fim/fha gene cluster: identification of a gene with sequence similarities to haemolysin accessory genes involved in export of FHA".
Stibitz, Scott, et al, *Journal of Bacteriology*, vol. 170, No. 7, 1988, pp. 2904–2913, "Genetic Analysis of a Region of the *Bordetella pertussis* Chromosome Encoding Filamentous Hemagglutinin and the Pleiotropic Regulatory Locus vir".
Domenighini, M., et al, *Molecular Microbiology*, vol. 4, No. 5, 1990, pp. 787–800, "Genetic characterization of *Bordetella pertussis* filamentous haemagglutinin: a protein processed from an unusually large precursor".
Locht, Camille, et al, *Molecular Microbiology*, vol. 9, No. 4, 1993, pp. 653–660, "The filamentous haemagglutinin, a multifaceted adhesin produced by virulent Bordetella spp.".

* cited by examiner

*Primary Examiner*—Rodney P Swartz
*Assistant Examiner*—Khatol Shahnan-Shah
(74) *Attorney, Agent, or Firm*—Nixon & Vanderhye P.C.

(57) ABSTRACT

A recombinant DNA containing a sequence (1) coding for a polypeptide heterologous to a filamentous haemagglutinin of *Bordetella* (Fha) fused within the reading frame to a sequence (2) located upstream from the first sequence. Sequence (2) codes for at least part of the Fha precursor, which part comprises at least the N-terminal region of a truncated mature Fha protein, which contains the interaction site of Fha and heparin and the secretion domain. This Fha protein is under the control of a promoter recognized by the cell polymerases of *B. pertussis* and is inserted into a *B. pertussis* cell culture, is expressed in the culture and excreted into the cell culture medium. The invention uses both the abilities of *Bordetella* and particularly *B. pertussis* to secrete or surface expose the heterologous polypeptide fused to the Fha portion corresponding to sequence (2), which does not appear to produce extracellular proteases, and the ease with which filamentous haemagglutinins can be isolated from other *Bordetella* proteins.

29 Claims, 16 Drawing Sheets

Figure 1:
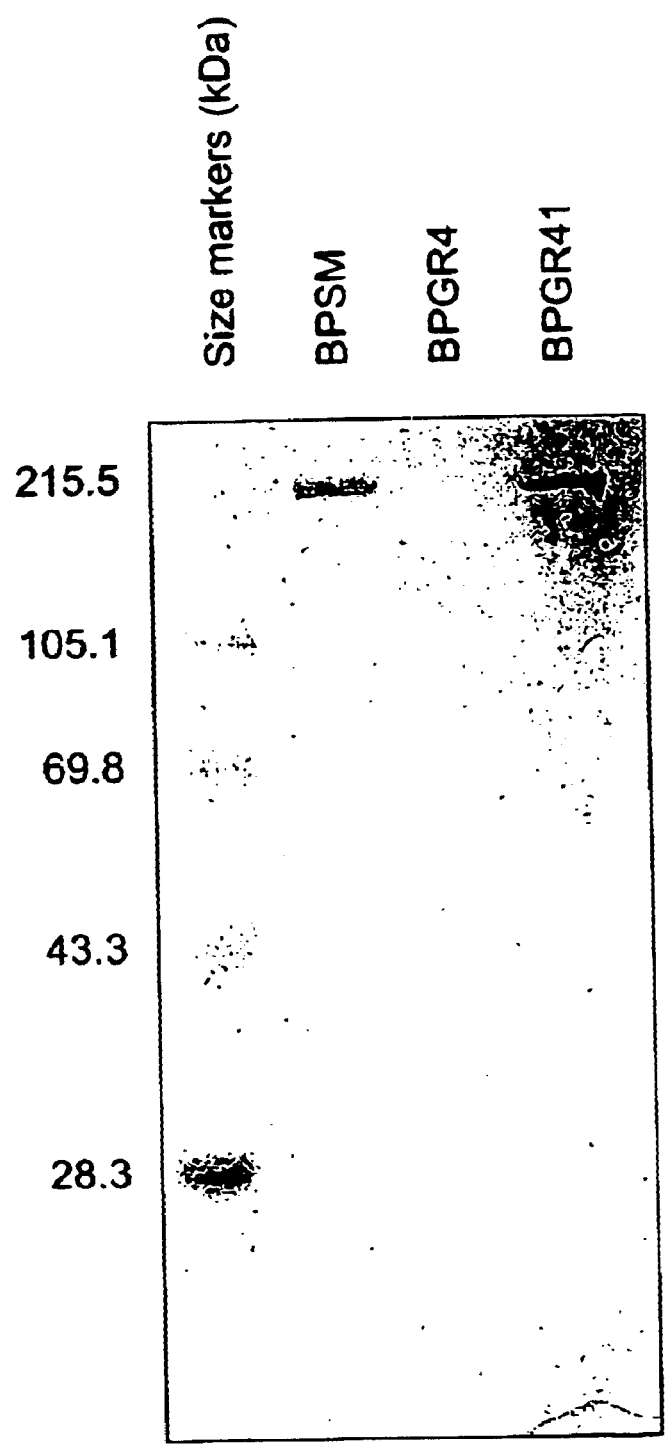

Il-6 in the bronchoalveolar lavages of OF1 mice infected with BPGR60

SEQUENCE LISTING

```
<160> NUMBER OF SEQ ID NOS: 12

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence:Primer

<400> SEQUENCE: 1
taggatccgg gccggggccc gaaaatctgt tagcc                            35

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence:Primer

<400> SEQUENCE: 2
taagatctcc cgggccccgg gaagggagtt gcagg                            35

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:Primer

<400> SEQUENCE: 3
taagatctcc atggctggcg agcat                                       25

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 4
taagatctcc gagctttctg ttg                                         23

<210> SEQ ID NO 5
<211> LENGTH: 32
<212> TYPE: DNA
<213> ORGANISM: Artificial Sequence
```

```
<220> FEATURE:
<223> OTHER INFORMATION: Description of Artificial Sequence:Primer

<400> SEQUENCE: 5
taaggatccc catggctggc gagcatatca ag                              32

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence:Primer

<400> SEQUENCE: 6
cctgtcgacc ctttcagaga ttcgctgatc atattgag                        38

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence:Primer

<400> SEQUENCE: 7
taaggatccc catggctggc gagcatatca ag                              32

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence:Primer

<400> SEQUENCE: 8
taaggatccc gaagggagtt gcaggcctgt t                               31

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 9
tttaaccgat gcggccgccg ttg                                        23

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence:Primer

<400> SEQUENCE: 10
tataagcttc gaacctgtac aggctggtc                                  29

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 11
tcaaagcttc gcgtggtcaa gcgcgaag                                   28
```

```
<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence:Primer

<400> SEQUENCE: 12
attaagcttc ccagggcttg gttcctcag                                       29
```

US 6,841,358 B1

RECOMBINANT PROTEINS OF FILAMENTOUS HAEMAGGLUTININ OF BORDETELLA, PARTICULARLY *BORDETELLA PERTUSSIS*, METHOD FOR PRODUCING SAME, AND USES THEREOF FOR PRODUCING FOREIGN PROTEINS OF VACCINATING ACTIVE PRINCIPLES

This application is a 371 of PCT/FR95/00512, filed on Apr. 19, 1995, which claims priority to French application No. 94/04651 filed on Apr. 19, 1994.

SUBJECTS OF THE INVENTION

As a result of the technology of genetic engineering it is, in principle, now possible to express any gene in a heterologous organism in order to make available unlimited quantities of a given protein for industrial or research purposes. Micro-organisms are very often used as hosts for the heterologous expression.

Paradoxically, in spite of the considerable progress observed during the last twenty years one of the problems which has slowed down the industrial use of recombinant proteins is linked to the difficulty of purifying these molecules which are usually concerted in the organism which synthesizes them. The purification of the recombinant proteins could be considerably simplified if the latter were secreted into the culture medium. The genetic manipulation of a micro-organism so that it secretes a recombinant protein requires knowledge of the molecular mechanisms which govern the metabolic pathways of secretion. These mechanisms are particularly complex in the Gram-negative bacteria in which any secreted protein must cross two lipid membranes before reaching the extracellular medium. Consequently, the Gram-negative bacteria secrete few proteins.

The secretion of proteins is simpler in the Gram-positive bacteria owing to the fact that the latter possess only a single lipid membrane. Unfortunately, these micro-organisms also usually produce extracellular proteases, harmful to recombinant proteins. The construction of Grim-positive bacteria deficient in proteases has consequently been a important area of research. However, this task has proved difficult since these micro-organisms often secrete many proteases and the deletion of the genes coding for these proteases diminishes the viability of the strains and consequently their usefulness for the expression of the heterologous genes. Hence, ideally, Gram-negative bacteria producing no or few extracellular proteases and possessing a very effective mechanism of secretion should be used.

The invention takes advantage both of the capacities of the *Bordetella*, and more particularly of *B. pertussis* which seems not to produce extracellular proteases, and the ease with which filamentous hemagglutinins can be isolated from those of the *Bordetella* synthesizing them in order, among other things, to solve the difficulties mentioned above.

*Bordetella pertussis*, the etiological agent of whooping cough, is a Gram-negative bacterium which produces and secretes several large proteins including the whooping cough toxin (about 107 kDa) and the filamentous hemagglutinin (Fha; about 220 kDa). The Fha is the major product of secretion, it can easily be detected by staining with Coomassie blue after electrophoresis of the culture supernatant.

The Fha is a protein of 220 kDa produced and secreted by *B. pertussis*. It is the major adhesin and the major product of secretion of this organism (for a review cf. Locht, C, Bertin, P., Menozzi, F. D. and Renauld, G (1993) Mol. Microbiol. 9, 653–660). The structural gene for Fha, called fhaB, has been cloned in several laboratories (Brown, D. R. and Parker, C. D. (1987) Infect. Immun. 55, 154–161; Relman, D. A., Domenighini, M., Tuomanen, E., Rappuoli, R., and Falkowo, S. (1989) Proc. Natl. Acad. Sci. U.S.A. 86, 2637–2641; Delisse-Gathoye, A-M, Locht, C., Jacob, F., Raaschou-Nielsen, M., Heron, I., Ruelle, J-L., DeWilde, M. and Cabezon, T; (1990) Infect. Immun. 58, 2895–2905) and codes for a precursor of about 367 kDa (Delisse-Gathoye et al., 1990; Domenighini, M., Relman, D., Capiau, C., Falkow, S., Prugnola, A., Scarlato, V. and Rappuoli, R. (1990) Mot. Microbiol. 4 787–800). The N-terminal part of this precursor corresponds to the mature part of the Fha and the C-terminal part is lost during the maturation and/or secretion of the protein.

Downstream from the fhaB gene there is a polycistronic operon responsible for the biogenesis of both the Fha and the fimbriae, also called agglutinogens (Locht, C., Geoffroy, M. C. and Renauld, G. (1992) EMBO J., 11.3175–3183). This operon contains four cistrons, the products of the first three of which are homologous to the accessory proteins and to the adhesin of the pili of several Gram-negative bacteria (Locht et al., 1992) and are implicated in the biogenesis of the fimbriae of *B. pertussis* and the product of the last of which is homologous to ShlB and HpmB and is implicated in the biogenesis of the Fha (Willems, R. J. L., Geuijen, C., van der Heide, H. G. J., Renauld, G., Bertin, P., van der Akker, W. M. R., Locht, C. and Mooi, F. R. (1994) Mol. Microbiol. 11, 337–347).

Furthermore, the N-terminal region of the Fha is homologous to the N-terminal regions of the hemolysins SHlA and HpmA of *Serratia marcescens* and *Proteus mirabilis*, respectively (Delisse-Gathoye et al., 1990). These hemolysins are secreted by these two micro-organisms and the secretion implicates the interaction of the product of the sh1B or hpmB gene with the N-terminal domain of ShlA and HpmA, respectively (Braun, V., Ondraczed, R. and Hobbie, S. (1993) Zbl. Bakt. 278, 306–315). Mutagenesis experiments on the fhaB gene have shown that the N-terminal domain of the Fha, homologous to the ShlA and HpmA, is also important for the biogenesis of the Fha (Willems et al., 1994) thus suggesting by analogy with the secretion systems of the hemolysins that the product of the fhaC gene interacts with the N-terminal domain and that this interaction is important in the process of the biogenesis of the Fha. The proteins HpmB, ShlB and FhaC are probably proteins of the outer membrane (Braun et al., 1993; Willems et al., 1994) and play a role in the secretion of the hemolysins and of Fha, respectively, across the outer membrane. In *B. pertussis*, blockage of the secretion through the outer membrane leads to the rapid degradation of the protein.

The Fha is a major adhesin of *B. pertussis* and expresses at least three types of binding activities (see Locht et al., 1993). Relman et al. (Relman, D., Tuomanen, E., Falkow, S., Golenbock, D., Saukkonen, K. and Wright, S.(1990) Cell 61, 1375–1382) have shown that a RGD sequence in the mature Fha is responsible for the interaction of this molecule with the integrin CR3 (AMβ2, CD11b/CD 18) of the macrophages. This interaction induces the internalization of the *B. pertussis* in the macrophages in which these organisms may survive.

The Fha may also interact with glycoconjugates and the recognition domain of the carbohydrates has been identified by Prasad et al. (Prasad, S. M., Yin, Y., Rodzinski, E., Tuomanen, E. I. and Masure, R. (1993) Infect. Immun. 61, 2780–2785) in the region 1141 to 1279 of the Fha, a little downstream from the RGD site. Menozzi et al. (Menozzi, F. D., Gantiez, C. and Locht, C. (1991) FEMS Microbiol. Lett. 78, 59–64) have shown that the Fha expresses an affinity for heparin and can be purified by chromatography on heparin-sepharose from the culture supernatant of B. pertussis. This interaction with sulfated glycosaminoglycans seems to play a role in the interaction of the micro-organisms with epithelial cells
(Menozzi, F. D., Mutombo, R., Renauld, G., Gantiez, C., Hannah, J. H., Leininger, E., Brennan, M. J. and Locht, C (1994) Infect. Immun. 62, 769–778).

The Fha is a good immunogen for the induction of IgAs in the respiratory tracts of the patient infected with B. pertussis (Zackrisson, G., Lagergard, T., Trollfors, B. and Krants, I (1990) J. Clin. Microbiol. 38, 1502–1505) and the presence of IgAs is still detectable long after the infection (Zackrisson, G., Arminjon, F., Krantz, I.,Lagergard, T., Sigurs, N., Taranger, J. and Trollfors, B. (1988) Eur.J. Clin. Microbiol. Infec. Dis. 7, 764–770). A long-lasting immune response to the Fha can also be observed in the mouse experimentally infected with B. pertussis by the nasal route (Amsbaugh, D. F., Li, Z.-M. and Shahin, R. D. (1993) Infect. Immun. 61, 1447–1452). A good immune response (both IgAs and IgG) to the Fha can also be obtained in the respiratory tracts of the mouse after intra-nasal vaccination with the purified Fha (Shahin, R. D., Amsbaugh, D. F. and Leef, M. F. (1992) Infect. Immun. 60, 1482–1488; Cahill, E. S., O'Hagan, D. T., Illum, L. and Redhead, K. (1993) FEMS Microbiol. Lett. 107, 211–216). It is possible that one or more of the binding activities expressed by the Fha is/are responsible for the mucosal immunogenicity of this molecule.

The invention takes advantage of the molecular mechanism of secretion of the Fha of Bordetella, particularly of B. pertussis, for the production of heterologous recombinant proteins or peptides from these organisms.

In one of these initial applications the invention permits, particularly under the conditions which will be described hereafter, the secretion of these heterologous recombinant peptides into the heterologous culture medium and, where applicable, the recovery of the heterologous part of this recombinant peptide when the latter constitutes the ultimate target of research. However, the objective of another variant of the invention is the exposure of the recombinant peptide at the surface of prokaryote cells, particularly for vaccination purposes.

The fusion of heterologous proteins or peptides with the Fha may indeed have a particularly useful application in the vaccination area. In fact, the Fha is capable of stimulating a significant mucosal immune response of long duration after natural infection in man or following intranasal immunization. This property is probably due to the specific binding activities of the Fha to the mucosa. A translational fusion of the Fha with an antigen could hence facilitate the presentation of this antigen at the nasal mucosa to allow the production of secretory immunoglobulins (IgAs). Such a strategy is particularly useful for vaccination against certain respiratory diseases and, when the mucosal immune system of the respiratory tracts communicates with that of other mucosa or more generally of other cells: epithelial cells, macrophages, etc. . . , this principle may be entended to many other infectious diseases against which it is important to develop mucosal immunity. Such an inexpensive type of vaccine could easily be administered by a nasal spray. This route of vaccination would hence eliminate the trauma caused by injection as well as the risk of destruction of the oral vaccines in the acidic environment of the stomach.

In what follows reference will be made to the drawings, the legends id to which are presented at the end of this description.

The invention relates first of all to the recombinant DNA containing a sequence (1) coding for a polypeptide heterologous with respective to a Fha of B. pertussis fused in the same reading frame to a sequence (2) placed upstream from the first, this sequence (2) coding for at least the N-terminal region of the mature protein of Fha which, when this latter is itself placed under the control of a promoter recognized by the cell polymerases of B. pertussis and introduced into a B. pertussis culture, is expressed in this culture under the control of this promoter and excreted into the culture medium.

In an extreme case, the sequence (2) of the above-mentioned recombinant DNA codes for the entire Fha precursor, for example that of B. pertussis (sometimes designated by the abbreviation FhaB). The incorporation of this recombinant DNA into a plasmid in particular and under the control of an adequate promoter in a B. pertussis cell then leads to the expression of the corresponding recombinant protein, a part of which is excreted completely into the culture medium, the other part also crossing the B. pertussis membrane but remaining attached to it. In this last case it will be seen in what follows that the recombinant protein, including the amino acid sequence corresponding to the heterologous polypeptides, is exposed at the surface of these cells.

The protein excreted into the culture medium may be purified further, in particular by a process consisting of placing the culture medium in contact with heparin immobilized on an insoluble support in order to form a heparin-Fha complex, from which the recombinant protein can then be recovered by dissociation of the complex.

In the subsequent description, it will be seen that the initial assays were performed in a B. pertussis strain BGR4, in which the largest part of the reading frame of the fhaB gene and its promoter had been deleted from the chromosome by two consecutive homologous recombination events. The recombinant DNA contained an EcoRI fragment of about 10 kb isolated from a clone which had been sequenced completely, in particular by Delisse-Gathoye et al., 1990. It is in comparison with the sequence described by these authors that the relative positions of some of the nucleotides in the corresponding B. pertussis chromosome are defined in the body of the present text, the first EcoRI site $E^a$ corresponding to position 1 and the second EcoRI site $E^b$ then occupying position 10035.

The translation initiation codon ATG is located downstream from the $E^a$ site (one of the three ATG codons at positions 253, 298 and 427, respectively), the corresponding promoter being intercalated between the $E^a$ site and the relevant initiation ATG. The precursor extends beyond the position of the $E^b$ site (position 11025).

As will be described in more detail in the examples, several recombinant DNAs were produced which contained in particular sequences all extending between nucleotide 1 and the nucleotide 10035 (BPGR41), 6292 (BPGR413), 5215 (BPGR48), 2841 (BPGR44), 1575 (BPGR412) and finally 907 (BPGR415), respectively. Corresponding restriction sites are indicated on FIG. 2B.

Figure 2A:
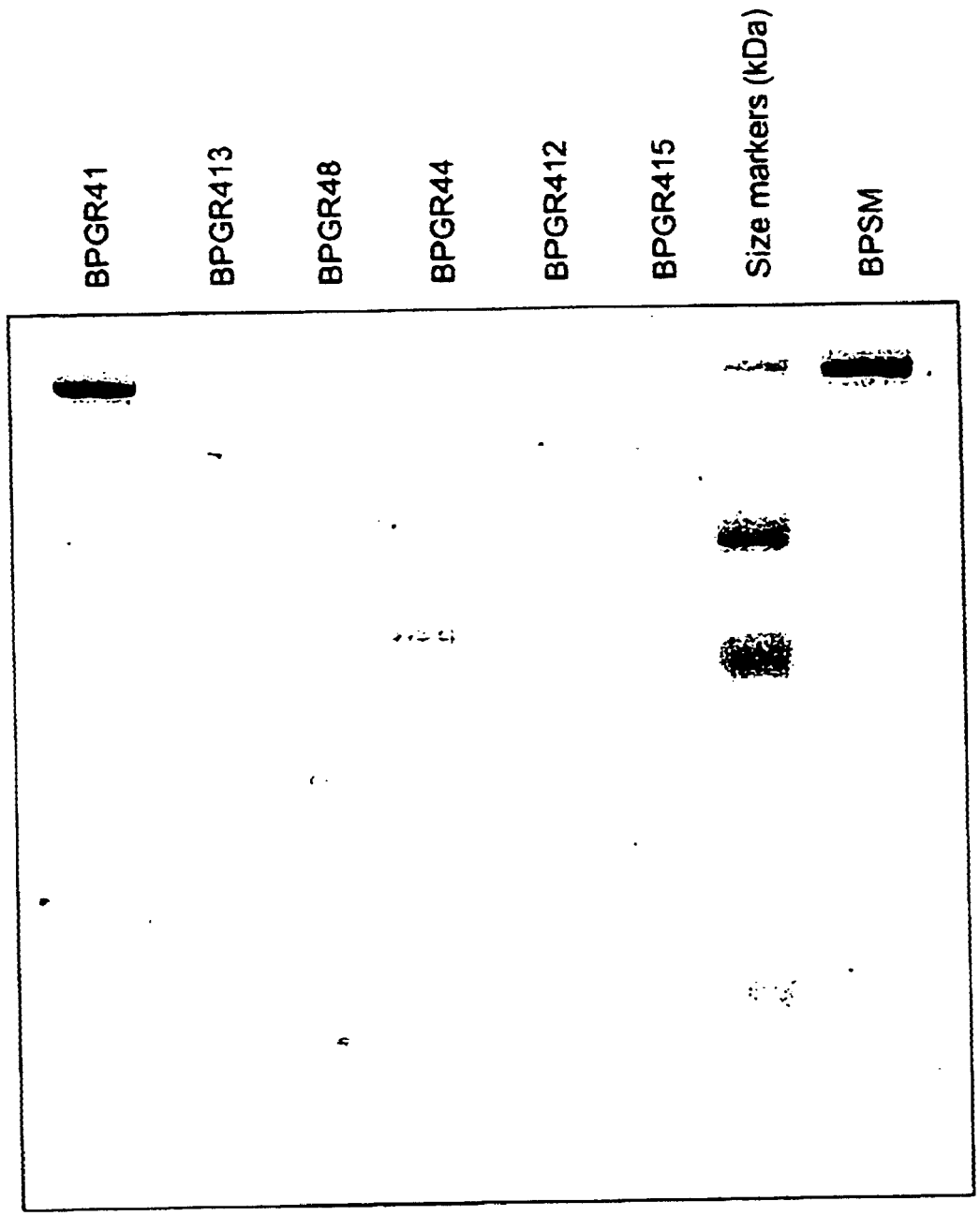
Figure 2B:
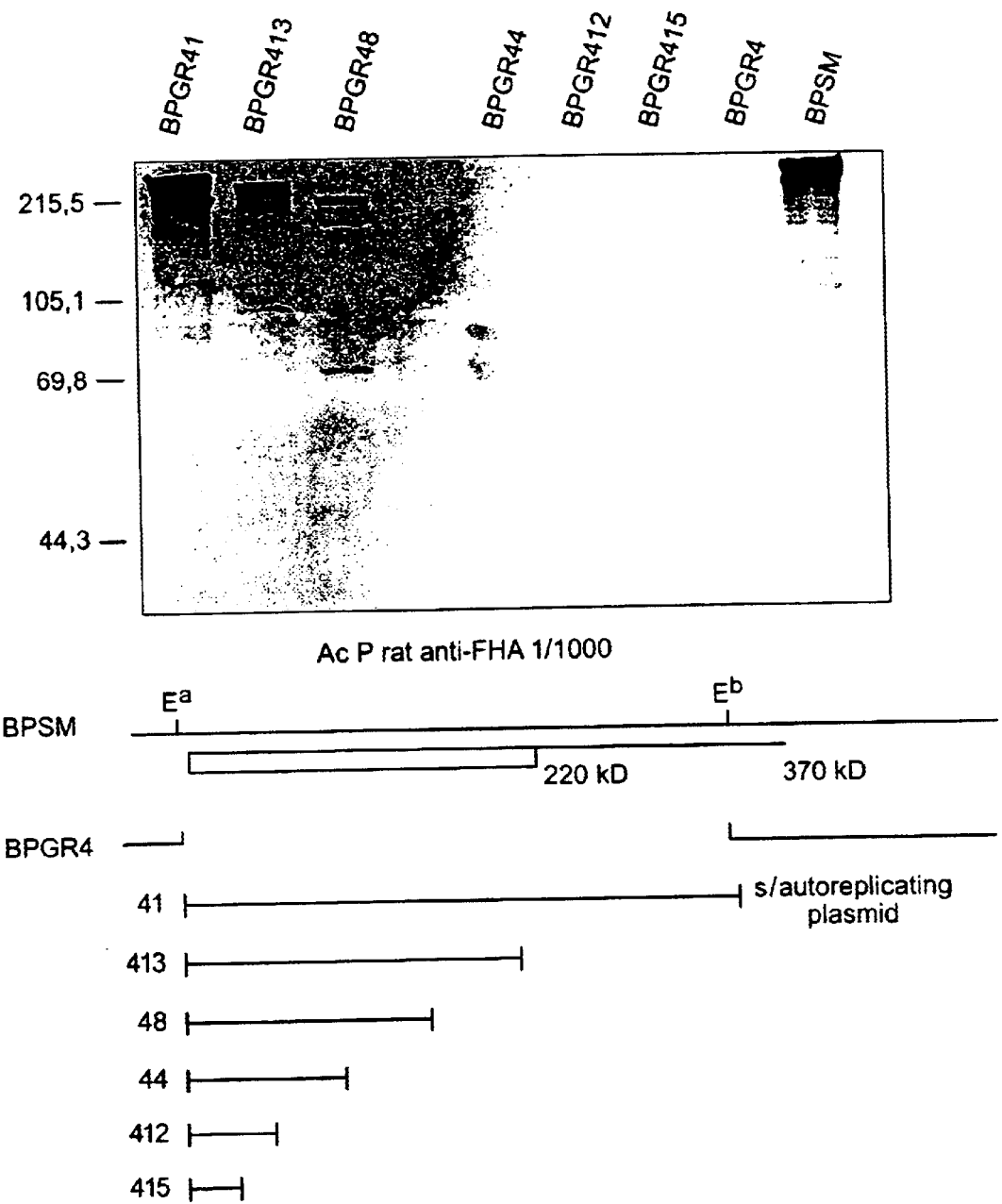
Figure 3A:
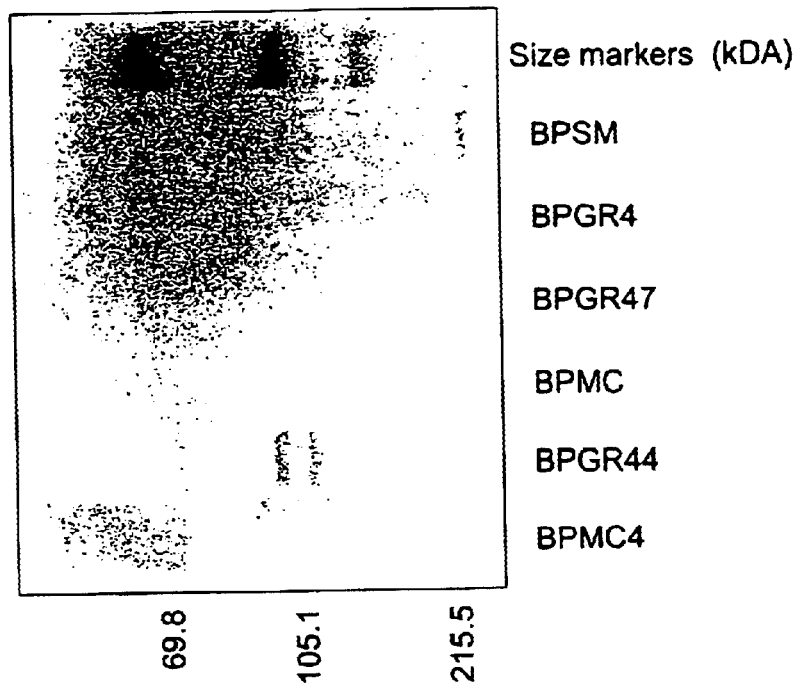
Figure 3B:
Figure 4:
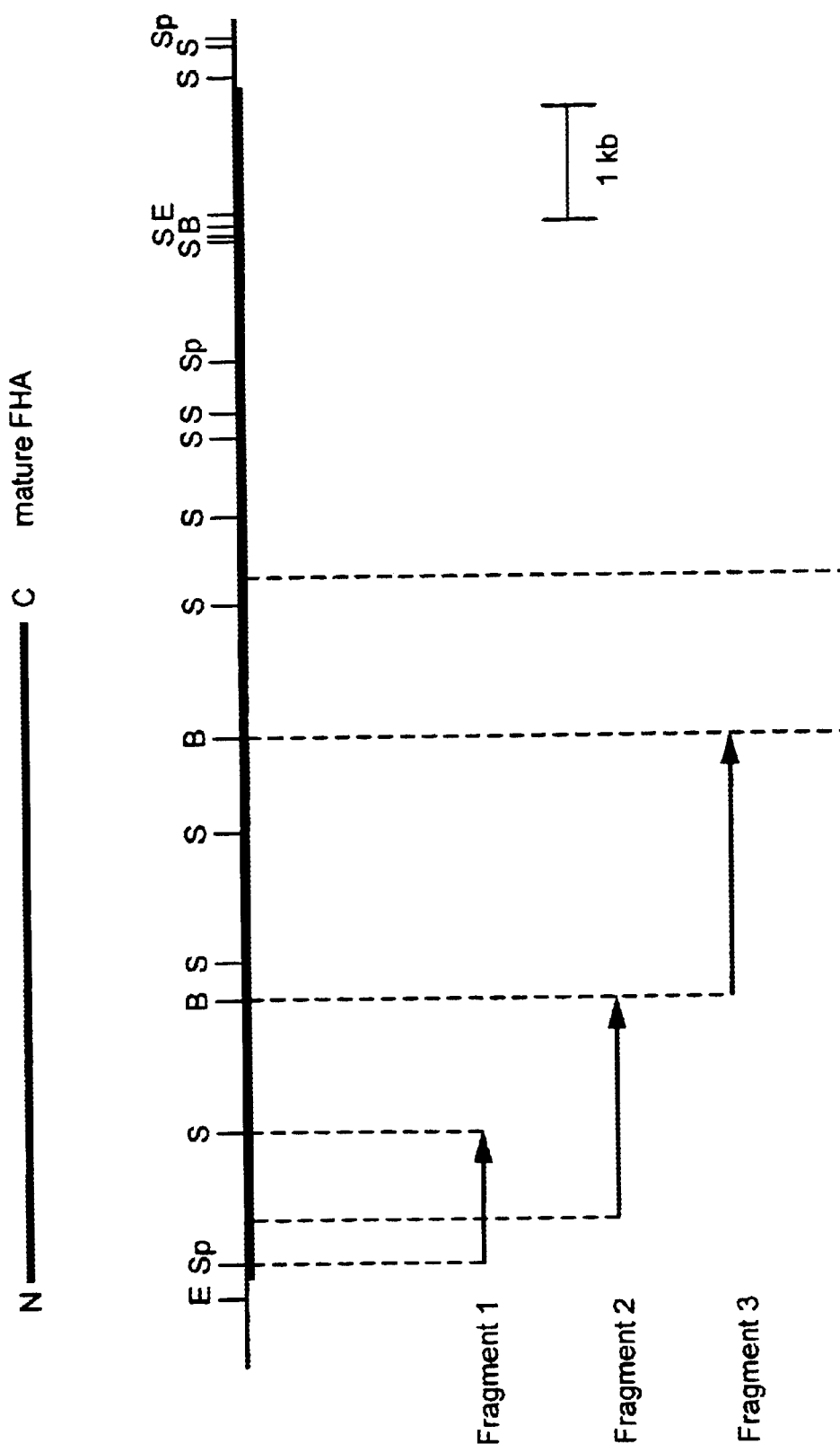

The following observations were made with respect to the expression of these fragments of decreasing size, before the later were recombined with a sequence coding for a heterologous peptide. As is shown in FIGS. 2A and 2B, considerable excretion of the peptide encoded in the peptide BPGR41 was obtained, an excretion which is reduced for the fragments contained in the plasmids BPGR413 and BPGR48, which contained no more than the sequence coding for almost all of the mature protein (BPGR413) and a truncated sequence coding for a polypeptide likewise truncated (BPGR48). These observations are reflected by the assays illustrated in FIG. 2B in which the expression products were detected by rat anti-Fha polyclonal antibodies. However, in this assay, the absence of detectable expression in the case of the plasmids containing shorter sequences is noted. On the other hand, using another system of measurement (staining with Coomassie blue: FIG. 2A), an upsurge of the expression with plasmid BPGR44 is recorded. Without there being a necessary correlation, it is noted that the part of the Fha sequence recognized by the major part of the polyclonal antibodies is not necessary for the production of excretion in the system which was used. When the truncated Fha sequence is shortened even more, a diminution of the excretion is again observed. Thus, the fragment contained in the plasmid BPGR412 is still expressed to a lesser degree even though no band is observed on FIG. 2 in the lane of the electrophoretic gel corresponding to the plasmid BPGR412. However, the placing of a corresponding culture in contact with immobilized heparin enabled an excreted fraction recognized by monoclonal antibodies recognizing specifically the N-terminal region of the Fha to be isolated.

It seems that sequences (2) included in the recombinant DNAs must, in every case, contain signals for the excretion of the sequence coding for the Fha and the N-terminal region homologous to the N-terminal regions of the hemolysins ShlA and HpmA of *Serratia marcescens* and *Proteus mirabilis*.

For the exploitation of one of the preferred embodiments of the invention, namely the production of a heterologous peptide and its recovery from the culture medium, it seems therefore that the extension of the sequence (2) from the N-terminus of the Fha towards its C-terminus should be selected so as not to exceed the length which would cause the transformation of *B. pertussis* with this recombinant DNA then placed under the control of a promoter capable of being recognized by *B. pertussis* to no longer permit the direct excretion of the recombinant protein then formed into the culture medium of this *B. pertussis*.

In the context of this embodiment, a preferred recombinant DNA is characterized in that the sequence (2) extends between the ATG corresponding to the initiation codon for the translation of the Fha to a C-terminal nucleotide beyond nucleotide 907 in the direction of the translation and preferably not beyond position 6292.

Although this assay is not decisive, it can still be asserted that a preferred recombinant DNA will be one which is characterized by the fact that it only reacts weakly with anti-Fha antibodies directed more particularly against the epitopes of the C-terminal part of the mature Fha, located beyond the nucleotide site 2841 in the sense of translation.

It is obvious that the recombinant sequence containing the sequences (1) and (2) may be constructed in any known manner depending on the nature of the final objective. Possibly, sequence (1) coding for the heterologous peptide will be flanked by short regions coding for pre-defined peptides forming specific cleavage sites for specific proteolytic enzymes, as a result of which the heterologous part of the recombinant polypeptide may be easily separated from the latter.

In another useful embodiment of the invention, the recombinant peptide can be used as vaccinating principle, the heterologous peptide sequence being endowed with immunogenic properties selected beforehand and, preferably, the part derived from the mature Fha protein comprising at least one of the specific attachment sites of the Fha to mucosa or more generally to other eukaryotic cells, particularly to epithelial cells or macrophages.

The use of recombinant DNA for the production of a heterologous polypeptide may be envisaged in prokaryotic cells other than *Bordetella pertussis* or even more generally than the *Bordetella*. Indeed, it should be noted that Stibitz, Weiss and Falkow reported DNAs of *Bordetella* containing the sequence coding for the precursor of the Fha and all of the regulatory genes, including the fhaC gene, i.e. the accessory gene whose expression product is also necessary for the expression of the Pha, can be expressed and exposed at the surface of the transformed *E. coli* bacteria when they are transported into *E. coli* (J. of Bacteriology (1988) 170, 2904–2913).

It is obvious that the invention thus relates to all cell cultures in which the Fha may be expressed. The invention thus relates more particularly to the cultures of cells belonging to a *Bordetella* species, in particular *B. pertussis*, provided that these cells also carry the fhaC gene which can be expressed in these cells.

The invention also relates to transformed cell cultures belonging to species other than *Bordetella* provided that they also contain a sequence coding for at least the part of the FhaC necessary for the expression of the sequence (2) in a form also expressable within the cells of this culture.

This is so for *E. coli* and, if necessary, provided minor adjustments are made allowing the expression of the recombinant DNAs of the invention in other Gram-negative bacteria, for example *salmonella, vibrio*, etc. . .

It should be noted that Willems et al. (1994) Mol. Microbiol. 11, 337–347 have completely sequenced a sequence coding for the FhaC protein. It is also obvious that the invention is not limited to recombinant DNAs containing a sequence coding for the Fha of *B. pertussis*. This latter may be replaced by any corresponding sequence isolable from other *Bordetella*, whether it be *Bordetella* infectious for man, in particular *B. parapertussis* or *B. bronchiseptica*, or also *Bordetella* infectious for animals, in particular the *Bordetella bronchiseptica* infectious for the dog or the pig.

The invention is in no way limited to the recombinant DNAs whose sequences (2) are restricted to truncated sequences of DNA coding for a Fha of *Bordetella*. As was seen above, the invention also relates to the recombinant DNAs containing longer sequences (2) whenever, on the contrary, the production of prokaryotic cells, in particular bacteria bearing exposed at their surface the expression product of the recombinant DNA defined above is to be attempted. The heterologous sequence (1) may either be incorporated even within the sequence coding for Fha, even FhaB or be fused to the mature Fha or the precursor with preservation of the corresponding reading frame.

In the case in which the host cell, if necessary after attenuation or inactivation, can be used as vaccine support, it will be realised that the invention provides novel varieties of vaccines comprising prokaryotic cells of this type bearing exposed at their surface the expression product of the recombinant DNA. Advantageously, both the amino acid sequence corresponding to the antigenic sites of the heterologous peptide, on the one hand, and one of the adhesion sites of the Fha protein to the mucosa or even to other eukaryotic cells such as epithelial cells or macrophages will be exposed at the surface of the bacteria in question.

Reference should be made to the European patent No. 0242243 filed on Jun. 3, 1987 for examples of the procedure which can be used to obtain the correct orientation Whereas in the case of the in vitro production of a recombinant protein or polypeptide prokaryotic cells may be transformed by a plasmid, it seems that for the construction of bacteria bearing the expression product of the recombinant DNA exposed at their surface it is preferable that the latter be incorporated into the chromosomal DNA of said cells under the control of a suitable promoter. All known procedures may be used for this purpose, such as the procedures of homologous recombination.

It is obvious that the sequence (1) may code for all desired antigenic sequences whether they be antigens of *Bordetella, Shigella, Neisseria, Borrelia*, etc. diphtheria, tetanus or cholera toxins or toxins, viral antigens, in particular of hepatitis B, hepatitis C, poliovirus or HIV, parasitic antigenic such as those of *plasmodium*, the Shistozoma, toxoplasms etc. Obviously, the examples given are in no way limiting.

Similarly, the cell hosts may be constituted by all attenuated or inactivated bacteria such as attenuated *shigella*, attenuated *E. coli* or attenuated *salmonella.*

However, as has been seen, any *Bordetella* fha may be used. Starting from a sequence coding for one of them, it is known that it is possible to detect corresponding sequences contained in the chromosomal DNA of other *Bordetella*, with the aid of appropriate probes for example.

The invention is of particular interest for the constitution of immunogenic or vaccination compositions designed for administration by mucosal contact, in particular for administration by the nasal route. The invention is hence of quite special interest for the prevention of infection by the respiratory tract or by tissues likely to be infected by these routes. The compositions of the type in question may be available in the form of aerosols, administrable as nasal sprays. The invention is applicable to both human and veterinary vaccination.

Other characteristics of the invention will also become apparent in the course of the description which follows of the constructions and biological assays which have been performed in the framework of the invention and which provide it with the required experimental support.

FIGURES

FIG. 1. Analysis by SDS-PAGE and staining with Coomassie blue of the culture supernatants of the *B. pertussis* strains BPSM, BPGR4 and BPGR41. The size markers and the unconcentrated culture supernatants of the three *B. pertussis* strains were loaded on to a SDS-polyacrylamide gel. After electrophoresis, the gel was stained with Coomassie blue as described by Sambrook et al.(1989). The molecular weights of the size markers are shown in the margin.

FIGS. 2A and 2B. Analysis by electrophoresis (A) and Western blot (B) of the culture supernatants of the *B. pertussis* strains BPGR41, BPGR413, BPGR48, BPGR44, BPGR412, BPGR415, BPGR4 and BPSM. After electrophoresis, the gel was stained with Coomassie blue as described for FIG. 1(A) or transferred to a nitrocellulose membrane and analyzed by Western blot as described by Delisse-Gathoye et al. (1990) with the aid of rat anti-FHA polyclonal antibodies at a dilution of 1/1000. The map of the constructions which are based on the different strains is shown. $E^a$ and $E^b$ represent the first and second EcoRI site of the fhaB gene, respectively (Delisse-Gathoye et al., 1990).

FIGS. 3A and 3B. Analysis by electrophoresis (A) and Western blot (B) of the culture supernatants of the *B. pertussis* strains BPSM, BPGR4, BPMC, BPGR44, BPGM47, BPMC4 and BPSM4 and the *B. parapertussis* PEP4 after electrophoresis, the gel was stained with Coomassie blue as described for FIG. 1(A) or analyzed by Western blot using a rat anti-FHA antiserum at a dilution of 1/500 (B) as described for FIG. 2.

FIG. 4. Restriction map of the different DNA fragments expressed as a fusion with the gene coding for MalF. The black line at the top shows the length of the fhaB portion which codes for the mature FHA. N and C designated the amino and carboxyl-terminal regions, respectively. The black line in the middle shows the length of the fhaB open reading frame. E, EcoRI; Sp. SphI; S, SalI; B, BamHI. The arrows show the length of the fragments expressed and the direction of their expression.

FIGS. 5A and 5B. Western blot analysis of the culture supernatants of the *B. pertussis* strains, BPSM, BPGR44, BPGR4 and BPJNI. After electrophoresis, the gels were analyzed by Western blot as described for the FIG. 2 by using the rat anti-FHA antiserum at a dilution of 1/500 (A) or a rat anti-peptide 190–211 antibody of Sm28GST at a dilution of 1/250 (B). The lane on the left of the gel (B) contains the purified recombinant Sm28GST.

FIG. 6. Western blot analysis of the culture supernatants and proteins associated with the cells of the *B. pertussis* strains BPSM, BPGR4, BPGR5 and BPGR6. The Western blot analysis of the proteins derived from the culture supernatants (lanes 5 to 8) or protein fractions associated with the cells (lanes 1 to 4) of the different *B. pertussis* strains BPSM (lanes 1 and 5), BPGR4 (lanes 2 and 6), BPGR5 (lanes 3 and 7) and BPGR6 (lanes 4 and 8) was performed as described for FIG. 2 by using the ant-FHA 12.1.9 monoclonal antibody (Delisse-Gathoye et al., 1990).

FIG. 7. Western blot analysis of the culture supernatants and proteins associated with the cells of the *B. pertussis* strains BPSM, BPGR5 and BPGR6. The Western blot analysis of the proteins derived from the culture supernatants and purified on a heparin-sepharose matrix (lanes 4 to 6) or protein fractions associated with the cells (lanes 1 to 3) of the different *B. pertussis* strains BPSM (lanes 1 and 4), BPGR5 (lanes 2 and 5) and BPGR6 (lanes 3 and 6) was performed as described for FIG. 2 by using a rabbit anti-Sm28GST antiserum diluted 200 fold.

FIG. 8. Western blot analysis of the culture supernatants of the *B. pertussis* strains BPSM, BPGR5 and BPGR6 purified on a heparin-sepharose column. The Western blot analysis of the proteins derived from the culture supernatants of the *B. pertussis* strains BPSM (lane 1), BPGR5 (lane 2) and BPGR6 (lane 3) after purification on a heparin-sepharose matrix was performed as described for FIG. 2 by using the anti-FHA 12.1.9 monoclonal antibody (Delisse-Gathoye et al., 1990).

FIG. 9. Western blot analysis of the culture supernatants and the proteins associated with the cells of the *B. pertussis* strains BPSM and BPGR60. The Western blot analysis of the proteins derived from the culture supernatants (lanes 1 and 3) or protein fractions associated with the cells (lanes 2 and 4) of the *B. pertussis* strains BPSM (lanes 3 and 4) and BPGR60 (lanes 1 and 2) was performed as described for FIG. 2 by using the anti-FHA 12.1.9 monoclonal antibody (Delisse-Gathoye et al., 1990).

FIG. 10. Western blot analysis of the culture supernatants and the proteins associated with the cells of the *B. pertussis* strains BPSM and BPGR60. The Western blot analysis of the proteins derived from the culture supernatants (lanes 1 and 3) or protein fractions associated with the cells (lanes 2 and 4) of the *B. pertussis* strains BPSM (lanes 1 and 2) and BPGR60 (lanes 3 and 4) was performed as described for FIG. 2 by using a rabbit anti-Sm28GST antiserum. Lane 5 contains the purified recombinant Sm28GST.

Figure 11A:
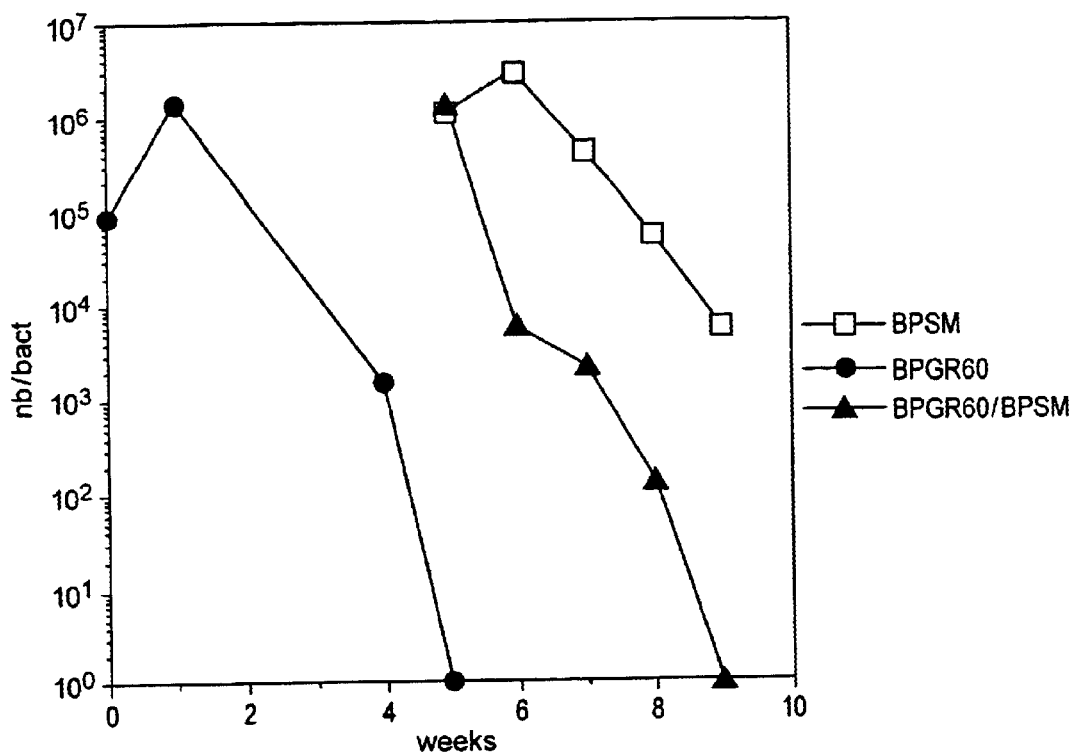
Figure 11B:
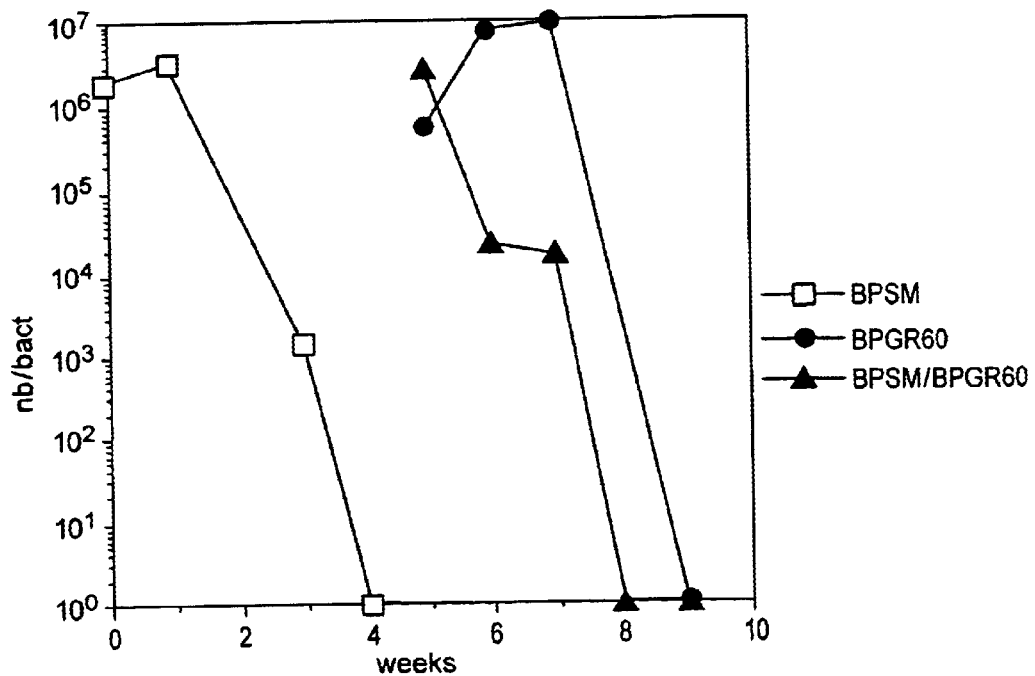

FIGS. 11A and 11B. Colonization of OF1 mice by *B. pertussis* BPGR60 and Tohama I. The OF1 mice were infected by the nasal route with the *B. pertussis* strains Tohama I (open squares), BPGR60 (full circles), BPGR60 and Tohama I (full triangles in A) or Tohama I then BPGR60 (full triangles in B). Three hours after infection, one group of mice was sacrificed and the number of viable *B. pertussis* per lung was estimated. The other groups of mice were analyzed one or more weeks after infection as shown in the Figure.

Figure 12A:
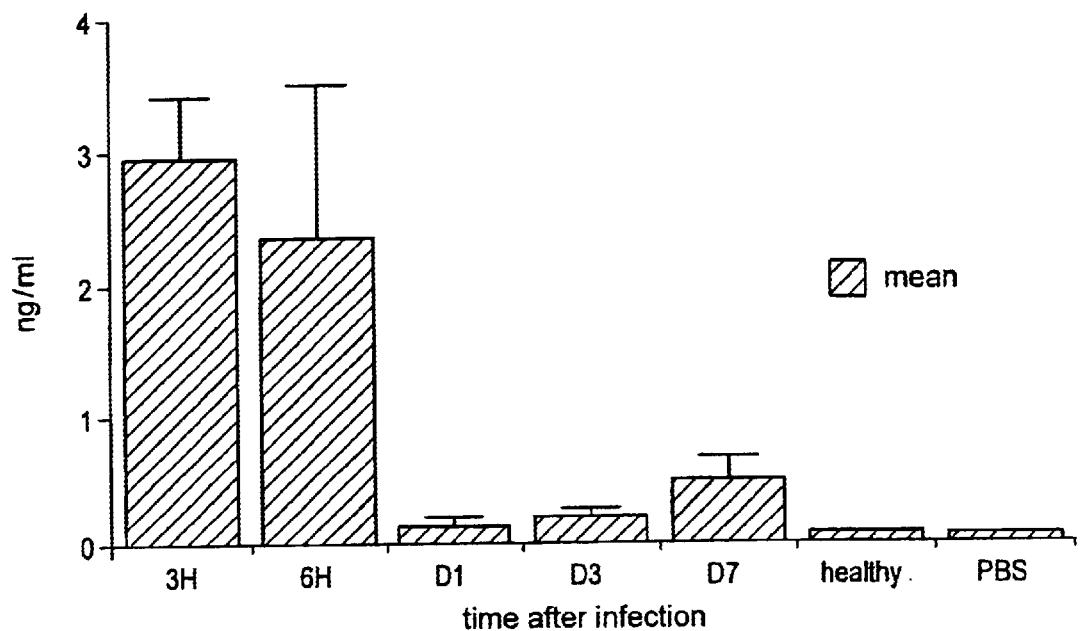
Figure 12B:
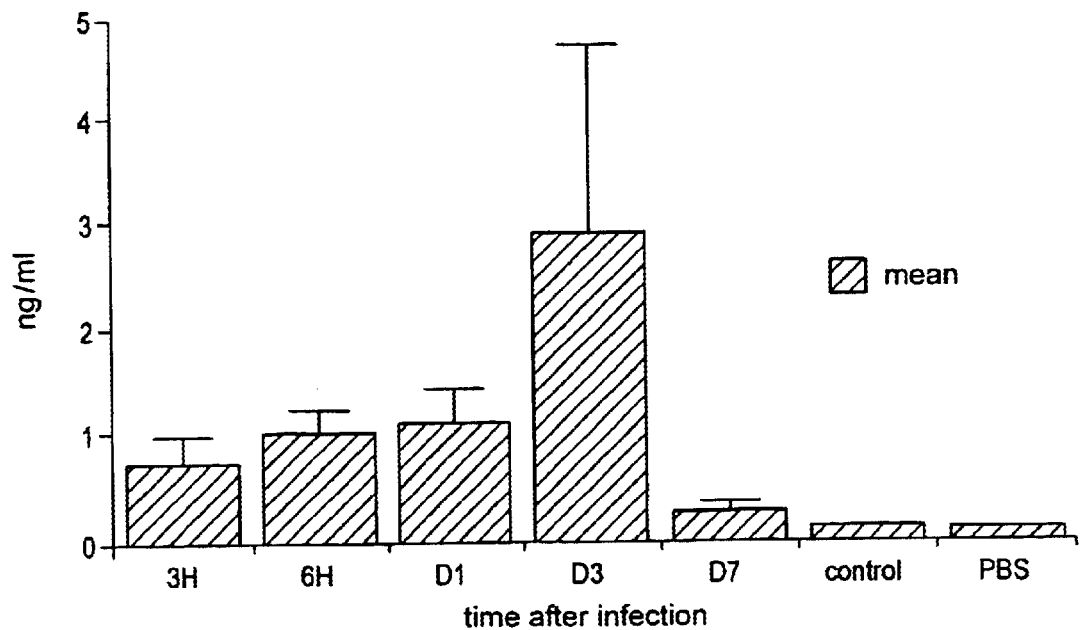

FIGS. 12A and 12B. Determination of TNF and Il-6 of the mice infected by *B. pertussis* BPGR60. TNF (A) and Il-6 (B) were determined in the mice uninfected (healthy) or infected with *B. pertussis* BPGR60 3 h, 6 h, 1 day, 3 days or 7 days after infection.

Figure 13A:
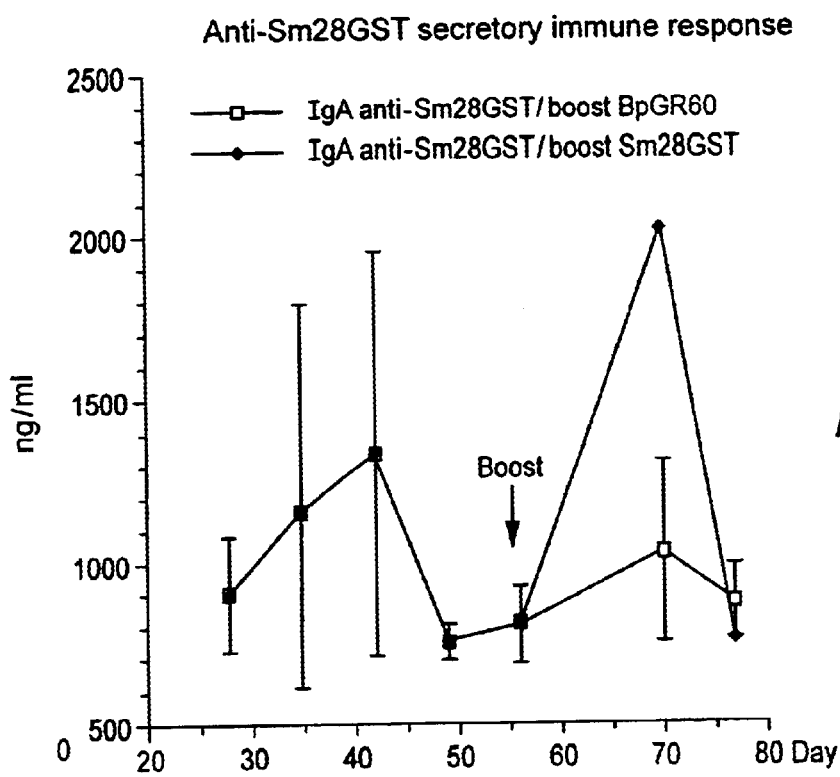
Figure 13B:
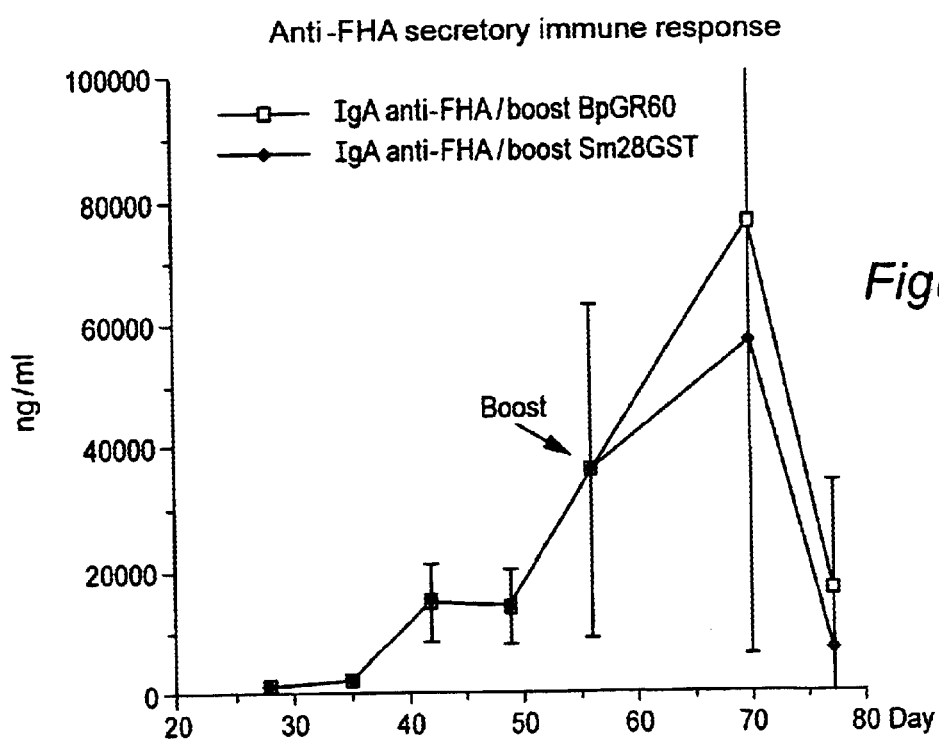

FIGS. 13A and 13B. Determination of anti-Sm28GST and anti-Fha IgA in the bronchoalveolar lavages of the OF1 mice infected by *B. pertussis* BPGR60. The OF1 mice were infected with *B. pertussis* BPGR60 by the nasal route. After infection, on the days indicated in the Figure, groups of mice were sacrificed and the anti-Sm28GST (A) and anti-Fha (B) IgA in their bronchoalveolar fluid were determined. On day 56 (in A) or 63 (in B), 20 μg of Sm28GST (full triangles) or a further dose of *B. pertussis* BPGR60 (full squares) were administered by the nasal route.

Figure 14:
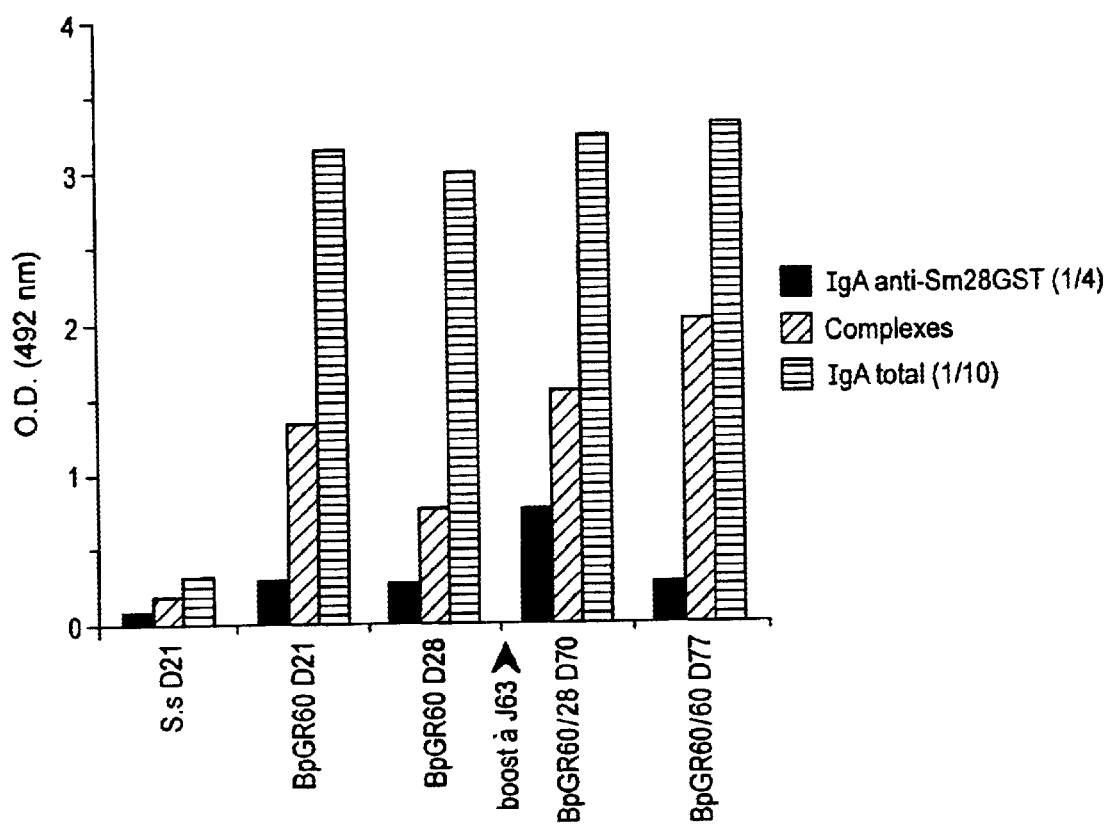

FIG. 14. Determination of IgA-Sm28GST complexes in the bronchoalveolar lavages of the mice treated as previously described in the legend to FIG. 13. The quantity of complexes (hatched columns) is shown in comparison with the free anti-Sm28GST (full columns) IgA and the total IgA (shaded columns).

Figure 15A:
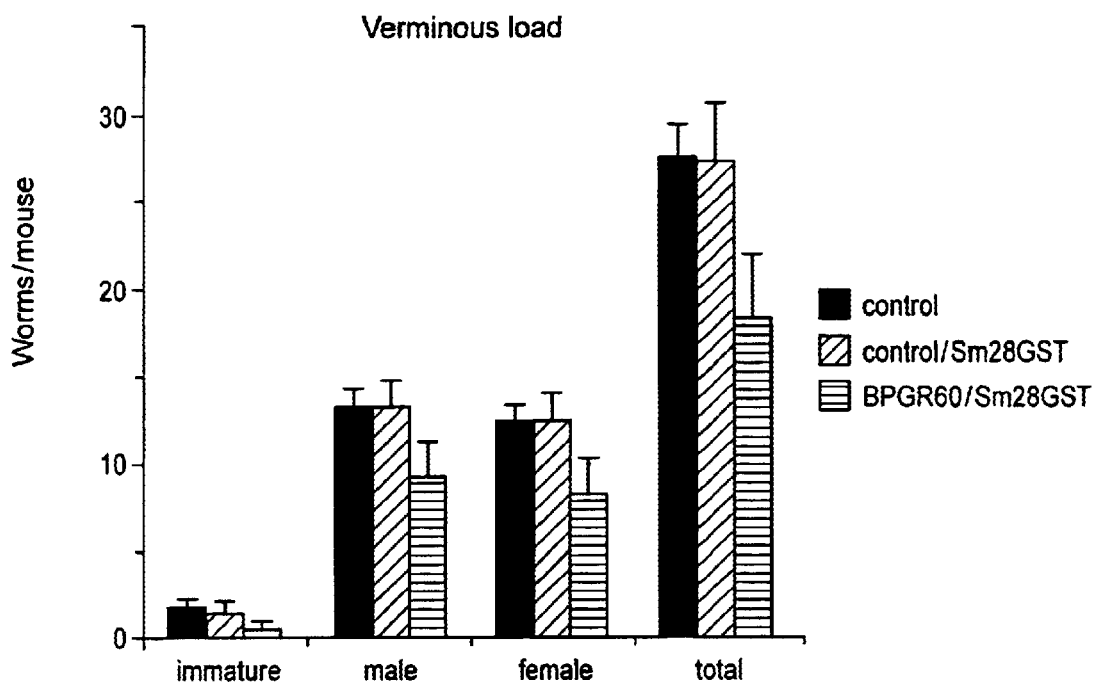
Figure 15B:

FIGS. 15A and 15B. Parasitic load observed after infestation by *S. mansoni* of OF1 mice previously immunized by BPGR60 and given a booster dose of free Sm28GST. The doses administered are identical with those used for the immunization experiments (FIG. 13). After 42 days the mice were sacrificed and the liver perfused for evaluation of the verminous load (A). The liver and intestines are chemically solubilized and the tissue eggs counted (B). Full column, untreated mice; hatched column, mice receiving only free Sm28GST on D63; shaded column, mice treated with BPGR60 (DO) and by free Sm28GST (D63).

EXAMPLES

I. Complementation of the *B. pertussis* strain BPGR4 by a Plasmid Derived from pBBR1 Containing the fhaB Gene.

In order to discover whether it is possible to complement a chromosomal mutation of the fhaB gene by an autoreplicating plasmid we used the *B. pertussis* strain BPGR4 (Locht et al., 1992), a strain derived from the *B. pertussis* wild-type strain Tohama I in which the EcoRI fragment of 10 kb containing most of the reading frame of the fhaB gene and its promoter has been deleted from the chromosome by two successive homologous recombination events. This strain does not produce FHA. Moreover, the 10 kb EcoRI fragment isolated from pRIT13202 (Delisse-Gathoye et al., 1990) and containing most of the fhaB gene was cloned into the EcoRI site of the plasmid pBBR122. This plasmid is a derivative of pBBR1 isolated from *Bordetella bronchiseptica* and described by Antoine and Locht (Antoine, R and Locht, C (1992) Mol. Microbiol. 6, 1785–1799). It contains a 1364 bp HhaI fragment derived from pBR328 (Soberon, X., Covarrubias, L. and Bolivar, F. (1980) Gene 9, 287–305) and conferring resistance to chloramphenicol inserted into the PvuI site as well as the commercial gene (Pharmacia) conferring resistance to kanamycin inserted at the AvaI site at position 1388.

The digestion of pBBR122 by EcoRI and the insertion of the fhaB gene in the form of the 10 kb EcoRI fragment inactivates the gene for chloramphenicol resistance but not that for resistance to kanamycin. The recombinant plasmid was called pBG1 and was introduced into *B. pertussis* BPGR4 by electroporation. This new strain of *B. pertussis* is called *B. pertussis* BPGR41. The analysis of the culture supernatants of *B. pertussis* BPSM, an $Sm^R$ derivative of the Tohama I strain (Menozzi et al., 1994), of *B. pertussis* BPGR4 and *B. pertussis* BPGR41 by means of SDS-polyacrylamide electrophoresis (SDS-PAGE) and staining with Coomassie blue (FIG. 1) as well as by Western blot by using rat polyclonal antibodies specific for the FHA show that pBG1 can effectively complement the fhaB mutation of *B. pertussis* BPGR4.

II. Progressive Deletions of the C-terminal Region of FhaB.

The primary product of the fhab gene, i.e. the FHA precursor, is called FhaB. Since the N-terminal region homologous to the hemolysins ShlA and HpmA is important for the biogenesis of the FHA (Willems et al., 1994), it was important to investigate the role of the C-terminal region of FhaB in the biogenesis of the FHA. Several deletions of the C-terminal region were obtained: pBG13 is the result of exchanging the 2.5 kb SphI/BamHI fragment of pBG4 for the 6 kb SphI/BglII fragment of pRIT13202 (Delisse-Gathoye et al., 1990); pBG8 is the result of the insertion of the 4.7 kb BamHI fragment in pBG4 digested by BamHI; pBG4 is the result of the digestion of pBG1 by BamHI and of its religation, thus this plasmid has lost the two BamHI fragments of 4.7 kb and 2.37 kb; pBG12 is the result of exchanging the 2.5 kb SphI/BamHI fragment of pBG4 for the 1.27 kb SphI/BamHI fragment of pUC18-3, pUC18-3 was generated exchanging the 15 bp SphI/SalI fragment of pUC18 for the 1.27 kb SphI/SalI fragment of pRIT13197 (Delisse-Gathoye et al., 1990); pBG15 is the result of the religation of the two PvuI fragments of 3.65 kb and 2.76 kb after digestion of pBG4 by PvuI,,thus generating the deletion of the 1.9 kb PvuI fragment. The plasmids pBG13, pBG8, pBG4, pBG12 and pBG15 were introduced into *B. pertussis* BPGR4 by electroporation which generated the *B. pertussis* strains BPGR413, BPGR48, BPGR44, BPGR412 and BPGR415, respectively.

The culture supernatants of these different strains were analyzed by SDS-PAGE and staining with Coomassie blue as well as by Western blot using rat anti-FHA polyclonal antibodies. The results are presented in FIG. 2 and show that in comparison with the *B. pertussis* strain BPSM and the *B. pertussis* strain BPGR41, the strains BPGR413 and BPGR48 produce much less FHA in the culture supernatant. On the other hand, the strain BPGR44 produces more of truncated and secreted FHA than the strain BPSM or the strain BPGR4 1. The strains BPGR412 and BPGR415 again produce less truncated FHA than the strain BPGR44, although the truncated FHA produced by BPGR412 is clearly visible in the culture supernatant. These experiments show that importance of the C-terminal region of FhaB in the biogenesis and/or secretion of the mature FHA, but they also show that a truncated FHA (for example in strain BPGR44) may be very efficiently secreted in the absence of the FhaB C-terminal region.

III. Importance of fhaC in the Biogenesis of the Truncated fHA Encoded in pBG4 and Secretion in *Bordetella parapertussis*.

Figure 5A:
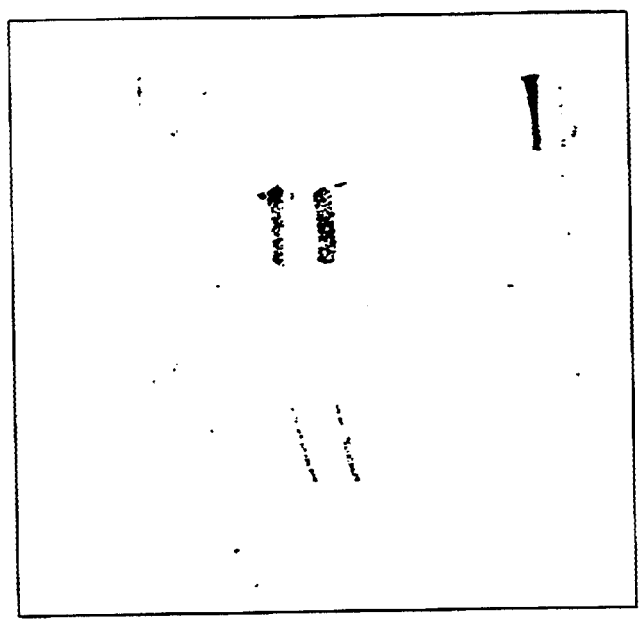
Figure 5B:
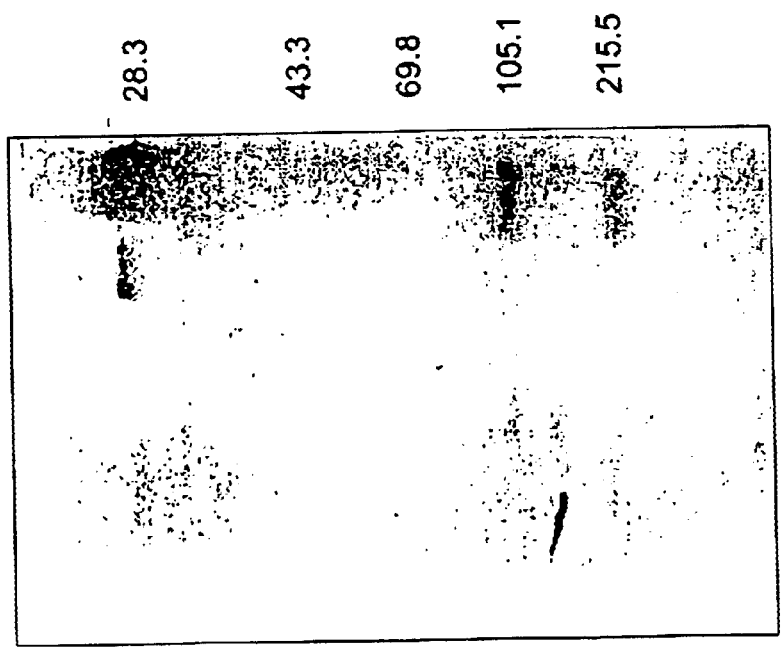

Since *B. pertussis* BPGR44 secretes the truncated FHA efficiently, it was important to know whether this secretion is always dependent on the product of the gene. pBG4 was thus introduced into the *B. pertussis* strain BPMC (Locht et al., 1992). This strain was characterized by a chromosomal deletion of the entire fhab gene and of the intergenic region between fhab and the accessory genes downstream, including fhaC. Hence it expresses neither fhaB, nor fhaC, nor the fimBCD genes (also called fhaDAE). The analyses resulting from SDS-PAGE/Coomassie blue staining of the culture supernatants of the *B. pertussis* strain BPMC (pBG4), called BPMC4, show that this strain does not produce extracellular truncated FHA. These results (FIG. 3) thus show that the expression of the fhaC gene is necessary for the extracellular production of the N-terminal region of the FHA. The importance of the N-terminal region of the FHA homologous to the hemolysins ShlA and HpmA (Delisse-Gathoye et al., 1990) for the secretion of the truncated FHA was studied by generating the *B. pertussis* strain BPGR47. This strain is a derivative of BPGR4 transformed with pBG7. This plasmid is the result of exchanging the 2.5 kb SphI/BamHI fragment of pBG4 for the SphI/BamHI fragment of pUC18-5 which is itself the result of the insertion of the approximately 1.27 kb SalI/BamHI fragment of the pRIT13120 (Delisse-Gathoye et al., 1990) into pUC18-4 digested by SalI and BamHI. The plasmid pUC18-4 is the result of the digestion of pUC18-3 by PstI and the religation on itself. This construction leads to an in-phase deletion of a PstI fragment of about 460 bp coding for the region of the FHA which is homologous to the hemolysins ShlA and HpmA. The analysis of the strain BPGR47 by means of electrophoresis and Western blot (FIG. 3) shows that the homologous region is also necessary for the secretion of the truncated FHA, as for that of the complete FHA.

In order to discover whether the truncated FHA could be produced and secreted by other species of the *Bordetella* genus, pBG4 was introduced into *Bordetella parapertussis* PEP (Nordmann, P., Francois, B., Menozzi, F. D., Commare, M. C. and Barois, A. (1992) Ped. Infect. Dis. J. 11, 248). The culture supernatant of the transformed strain was analyzed by means of SDS-PAGE and the result (FIG. 3) indicates that *B. parapertussis* can also secrete the N-terminal region of the FHA of *B. pertussis*, which suggests that *B. parapertussis* also expresses all accessory gene which corresponds to fhaC.

Finally, pBG4 was introduced into the *B. pertussis* strain BPSM and the analysis of the culture supernatant of the *B. pertussis* strain BPSM (pBG4), called *B. pertussis* BPSM4, shows that the product ion and secretion of the truncated FHA does not affect the production and secretion of the natural FHA and vice versa (FIG. 3). The system of secretion thus does not seem to be saturated by the expression of the fhaB gene.

IV. Identification of the Heparin Binding Site and Purification of the Truncated FHA on Heparin-Sepharose.

The FHA of *B. pertussis* can interact with heparin and be purified on heparin-sepharose (Menozzi et al., 1991). In order to know whether this interaction involves a site different from that which is responsible for the binding of the FHA to the CR3 integrins (Relman et al. 1990) or that responsible for the binding of the FHA to other glycoconjugates (Prasad et al., $1993)_p$ various DNA fragments covering altogether the entire fhab region which codes for the mature FHA were expressed as a fusion with MalE (a "maltose-binding protein") by using the expression system marketed by New England Biolabs (Beverly, Mass., USA). The various fragments expressed as a fusion with the gene coding for MalE are shown in FIG. 4. All of the fusion proteins were purified by chromatography on an amylose resin from a total lysate obtained after sonication of about 600 ml of a culture of *Escherichia coli* TG1 transformed by the different recombinant plasmids.

The recombinant proteins purified on amylose as well as MalE and the purified FHA were chromatographed on 3 ml of heparin-sepharose equilibrated with 100 ml PBS ("Phosphate Buffered Saline"). 40 ml of the different samples were adjusted beforehand to a concentration of 5 μg/ml in PBS +5 mM maltose, loaded on to the heparin-sepharose column and washed with PBS +5 mM maltose. The bound proteins were then eluted with PBS+0.5 M NaCl. The quantity of proteins in the fraction retained and eluted with PBS +0.5 M NaCl and that of the proteins not retained were compared to that of the total proteins loaded on to the column. The SDS-PAGE analysis of the different fractions was used to confirm that the proteins do indeed correspond to the expected fusion polypeptides. The results indicate that only fragment 2 (FIG. 4) codes for a polypeptide which is significantly retained on heparin-sepharose. Since fragment 1 (FIG. 4) does not code for a polypeptide retained on heparin-sepharose and since this fragment partially overlaps fragment 2, this suggests that the region of the FHA which interacts with heparin is located between the residues 441 and 863, in accordance with the numbering suggested by Delisse-Gathoye et al., (1990). This region contains most of the "A repeats" and two "B repeats" (Locht et al., 1993) suggesting that one or more of these "repeats" might be responsible for the binding between the FHA and heparin.

The truncated FHA produced and secreted by the *B. pertussis* strain BPGR44 contains the entire region encoded in the fragment 2 (FIG. 4) and thus would be expected to bind to heparin. The culture supernatant of this strain was thus chromatographed on heparin-sepharose and eluted with PBS +0.5 M NaCl. The analysis by SDS-PAGE and staining with Coomassie blue of the different protein fractions shows that the entire truncated FHA produced and secreted by the strain BPGR44 is retained on heparin and can be purified on heparin-sepharose by a procedure identical with that used for the purification of the natural FHA (Menozzi et al., 1991).

V. Production and Secretion of Heterologous Peptides as a Fusion with the Truncated FHA in *B. pertussis* and Purification on Heparin-Sepharose.

The efficient system of secretion of the FHA in *B. pertussis* was then used to secrete heterologous peptides in this organism. The model peptide used in this example is that which corresponds to the region 190–211 of the 28 kDa glutathione-S-transferase (Sm28 GST) of *Schistosoma mansoni* (Xu, C-B., Verwaerde, C., Gras-Masse, H., Fontaine, J., Bossus, M., Trottein, F., Wolowczuk, I., Tartar, A. and Capron, A. (1993) J. Immun. 150, 940–949). Two synthetic oligonucleotides with the following sequence: 5' TAGGATCCGGGCCGGGGCCCGAAAATCTGTTAGCC 3' (SEQ ID NO:1) and 5' TAAGATCTCCCGGGCCCCGGGAAGGGAGTTGCAGG 3' (SEQ ID NO:2) phosphorylated by standard methods (Sambrook, J., Fritsch, E. F. and Maniatis, T. (1989) Molecular Cloning: A laboratory manual, 2nd edition, Cold Spring Harbor Laboratories, Cold Spring Harbor, N.Y.) and used to amplify the region coding for the peptide 190–211 by means of the PCR. After amplification, the fragment was digested by BamHI and BglII and inserted into the BamHI site of pBG4. The recombinant plasmids were analyzed by restriction in order to discover the orientation of the oligonucleotide insert. A plasmid containing the oligonucleotide insert in the sense of the expression of the FHA, called pNJ1, was then purified and introduced into *B. pertussis* BPGR4 by means of electroporation. This recombinant strain is called BPNJ1 and its culture supernatant was analyzed by means of SDS-PAGE/Coomassie blue straining and Western blot by using polyclonal antibodies directed against the peptide 190–211 of Sm28GST. The results shown in FIG. 5 indicate that the strain BPNJ1 efficiently secretes the peptide 190–211 of S6GST as a fusion product with the truncated FHA and that this peptide restrains its antigenicity.

The culture supernatant of the BPNJ1 strain was then chromatographed on heparin-sepharose in the presence of PBS. The elution was performed in PBS +0.5 M NaCl. The analysis by SDS-PAGE and staining with Coomassie blue shows that all of the fusion protein is restrained on the column and may be eluted with PBS +0.5 M NaCl.

VI. Stability of pNJ1 in *B. pertussis* BPNJ1.

In order to determine the stability of pNJ1 in *B. pertussis* BPNJ1, the strain was incubated on solid medium in the absence of antibiotics. After 4 days of incubation at 37° C., 20 colonies were inoculated in liquid medium with and without kanamycin. After incubation for 4 days at 37° C., the count of colonies resistant to kanamycin in comparison to those which are not resistant to kanamycin indicates that all of the colonies bad retained resistance, showing that pNJ1 is stable in *B. pertussis* BPNJ1 in the absence of selection pressure. The plasmid content of 6 resistant colonies was analyzed by a rapid method of analysis (Baulard, A., Bertin, P., Dartois, V. and Locht, C. (1994) Math. Mol. Cell . Biol. 4, in press) and the result shows that all of the 6 colonies contained the pNJ1 plasmid.

Five OF1 mice were then infected intranasally with *B. pertussis* BPNJ1. About $10^6$ cfu ("colony forming units") per mouse were instilled nasally. After 7 days, the lungs of these mid were excised and the *B. pertussis* contained in the lungs were spread on a solid medium with or without kanamycin. After culture for 4 days at 37° C., the number of hemolytic bacteria resistant to kanamycin was compared to the number of hemolytic bacteria sensitive to kanamycin. The result shows that about 95% of the bacteria had lost the resistance to kanamycin.

Taken together, these results show that pNJ1 is very stable in *B. pertussis* in vitro but relatively unstable in vivo.

VII. Construction of the *Bordetella pertussis* Strain BPGR5, producing the Sm28GST of *S mansoni* fused to the FHA.

In order to determine whether a heterologous protein can be produced by fusion with the whole FHA, a fragment containing the entire cDNA of the Sm28GST together with its termination codon was fused to the reading frame of the fhab gene so that this frame is interrupted just after the insertion of the gene coding for the Sm28GST. A 0.68 kb BglII fragment containing the cDNA of the Sm28GST was amplified by PCR from the clone TG10, a derivative of the phage lambda gt10 (Pierce, R., Khalife, J., Williams, D., Kanno, R., Trottein, F., Lepresle, T., Sabatier, J., Achstetter, T. and Capron, submitted for publication) by using the following oligonucleotides: 5' TAAGATCTCCATGGCTGGCGAGCAT 3' (SEQ ID NO:3) and 5' TAAGATCTCCGACTTTCTGTTG 3' (SEQ ID NO:4) After digestion of the amplified fragment by the enzyme BglII it was cloned in the plasmid pRIT13202 (Delisse-Gathoye et al., 1990) previously digested by BglII and dephosphorylated. The recombinant plasmid is called pUC8-A. After digestion of pUC8-A by EcoRI, the 10.68 kb fragment is inserted into the EcoRI site of the mobilizable plasmid pGR5, a derivative of the plasmid pSS1129 bearing the 5' and 3' flanking regions of the fhab gene (Locht et al., 1992). The resulting plasmid (called pGR53) is transferred into the *E. coli* mobilizing strain SI7-1 for conjugation with *B. pertussis* (Simon, R., Priefer, U. and Puhler, A (1983) Bio/Technology 1, 784–791).

In order to introduce the genetic construction in a directed manner to the fhaB chromosomal locus, the *E. coli* strain SI7-1 (pGR53) is crossed with *B. pertussis* BPGR4. Since this strain lacks the major part of the fhab structural gene, the homologous double recombination events are forced to the flanking regions of this gene. After conjugation, the two recombination events are selected successively on selective media as previously described (Antoine, R. and Locht, C. (1990) Infect. Immun. 58, 1518–1526).

In brief, *E. coli* SI7-1 (pGR53)($Sm^S$, $Gen^R$, $Nal^S$) is crossed on a solid Bordet-Gengou (BG) medium with *B. pertussis* BPGR4 ($Sm^R$, $Gen^S$, $Nal^R$). After conjugation for 6 hours, the transconjugants are selected on a selective medium (BG+gentamycin+nalidixic acid). The resistance to gentamycin is supplied by the plasmid pGR53 and that to nalidixic acid is borne by the chromosome of the *B. pertussis* strain BPGR4. About 50 isolated colonies are then purified on the BG+gentamycin+nalidixic acid medium. In order to determine whether the $Gen^R$ clone has indeed been integrated into the plasmid pGR53, the transconjugants are replica-plated on the selective medium BG+streptomycin, then BG+gentamycin+nalidixic acid. The colonies having integrated the plasmid pGR53 are sensitive to streptomycin (the character of sensitivity to streptomycin being dominant to that of resistance). The $Gen^RSm^S$ transconjugants are then spread on the selective medium BG+streptomycin to select for the second recombinational event corresponding to the excision of the integrated plasmid. If this "crossinig-over" occurs at the same locus as the first time, the initial construction corresponding to the strain BPGR4 is found. If the second "crossing-over" takes place in the other recombinogenic region, the construction is integrated into the genome of *B. pertussis*. The excision of at the plasmid having provided the construction is checked by the appearance of the $Sm^RGen^S$ phenotype.

The candidate clones resistant to streptomycin and bearing the desired allelic exchange are identified by hybridization on colonies with a probe corresponding to the 0.68 kb BglII fragment described above. The chromosomal integrity at the junction of the flanking regions is confirmed after analysis of the genomic DNA by Southern blot.

The antigenicity of the heterologous fusion protein was demonstrated by Western blot analysis after separation by SDS-PAGE using a 10% gel. The protein fraction derived from the culture supernatant and that associated with the cells after growth of the recombinant bacteria in liquid culture in the Stainer-Scholte medium were analyzed. The fusion protein is identified in the protein fractions with polyclonal antibodies directed against the FHA, monoclonal antibodies directed against the FHA (Delisse-Gathoye et al., 1990), rat polyclonal antibodies directed against the truncated FHA, rabbit polyclonal antibodies directed against the Sm28GST and rat polyclonal antibodies directed against the peptide 190–211 of the Sm28GST. The anti-FHA antibodies were exhausted previously against a total lysate of the *B. pertussis* strain BPGR4 whereas the anti-Sm28GST antibodies were exhausted against a total lysate of the *B. pertussis* strain BPSM.

The fusion protein is detected in the protein fraction associated with the cells of the BPGR5 strain in which a protein band (doublet) slightly larger than the FHA reacts with both anti-FHA antibodies (FIG. 6) and anti-Sm28GST antibodies (FIG. 7). The genetic fusion is thus well expressed in this new heterologous expression system. Degradation products (characteristic of the FHA) are also observed in the protein fraction associated with the cells. However, no polypeptide is immunodetected in the crude culture supernatant, indicating that the fusion protein is not produced efficiently in a secreted form.

Figure 8:
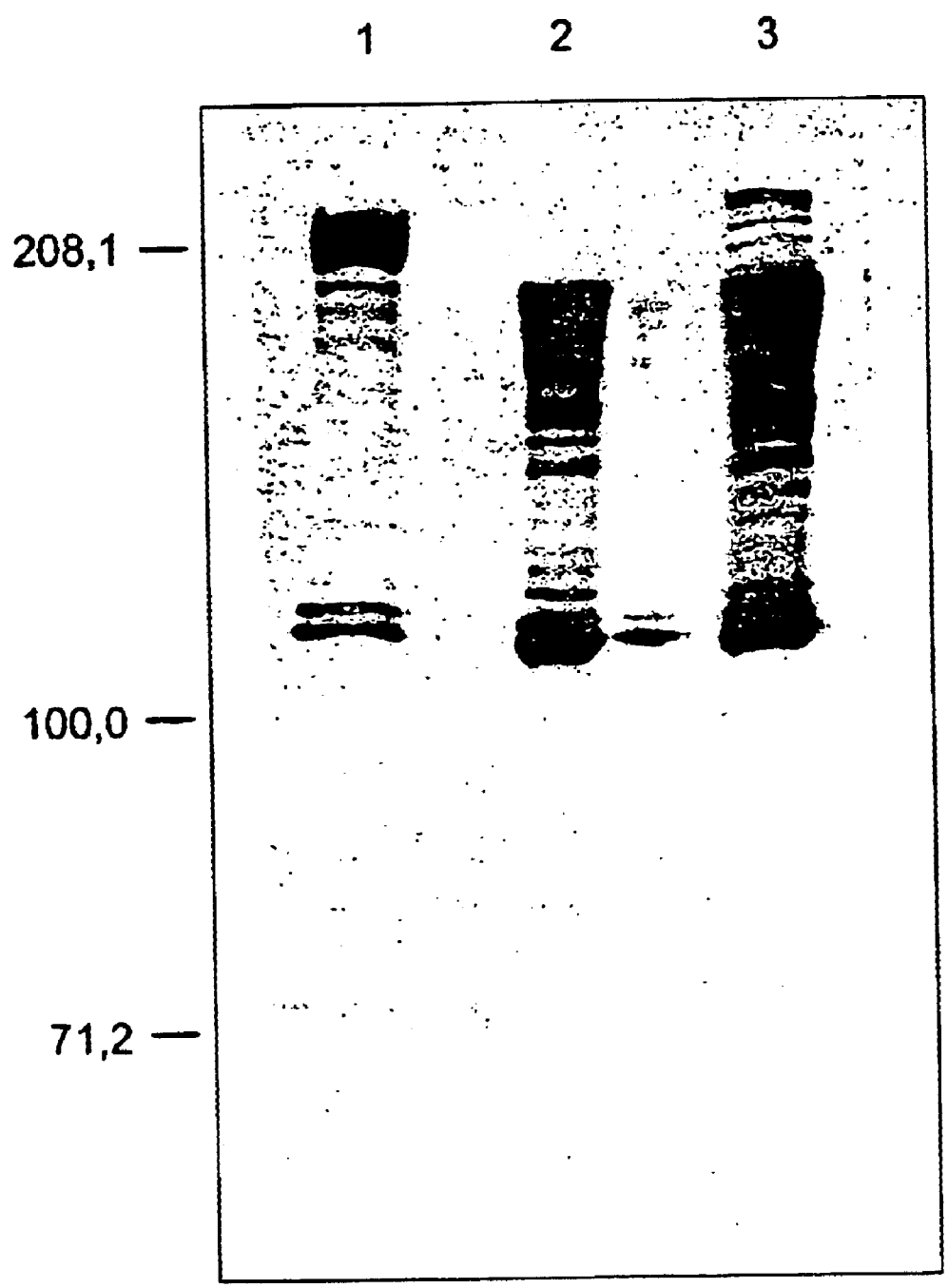

When the *B. pertussis* strain BPGR5 is cultured for more than 48 hours and the supernatant of this culture in the stationary phase is concentrated on a heparin-sepharose column, a secretion product is detectable (FIG. 8). It corresponds to a cleavage product of the fusion protein since it only reacts with the anti-FHA antibodies and not with the anti-Sm28GST antibodies. It thus seems probable that in this construction the portion of the Sm28GST molecule inserted at the end of the incomplete mature FHA remains attached to the inside of the outer membrane of the bacterium since it is not possible to release the complete fusion protein into the culture supernatant.

VIII. Construction of the *B. pertussis* Strain BPGR6, Producing a Truncated Sm28GST of *S. mansoni* Fused to the FHA.

For better exposure of the heterologous antigen it seemed to us more judicious to conserve the region of the FHA downstream from the insertion of the Sm28GST molecule in order in this way to express the entirety of the precursor and facilitate the export of the fusion protein through the two membranes of *B. pertussis*. For this reason, the reading frame of the fhaB gene is conserved after the insertion of the antigen or heterologous peptide into the following constructions.

For the construction of the *B. pertussis* strain BPGR6 we used a fragment containing three quarters of the cDNA of Sm28GST such that the reading frame of fhaB is maintained after insertion of the gene coding for a Sm28GST truncated by deletion of the C-terminus end of the gene. The gene coding for the truncated Sm28GST corresponds to the 0.5 kb BglII-BclI fragment. This fragment was isolated from the 0.68 kb BglII fragment and digestion with BglII and BclI. The 0.5 kb fragment was then inserted into the plasmid pRIT13202 (Delisse-Gathoye et al., 1990) digested by BglII and BclI, thus eliminating 0.1 kb of the reading frame of fhab. The plasmid thus obtained is called pUC8-F. The 10.4 kb EcoRI fragment was then isolated from pUC8-F and inserted into pGR5 (Locht et al., 1992) previously digested with EcoRI. The resulting plasmid pGR54 is then introduced into the *E. coli* strain S17-1.

The *E. coli* strain S17-1 (pGR54) is then crossed with *B. pertussis* BPGR4 in order to integrate the construction in the chromosomal fhaB locus as described in Example VII. After selection of the recombination events and analysis by Southern blot, the *B. pertussis* strain BPGR6 is retained. This strain is thus a derivative of *B. pertussis* BPSM with a deletion of 0.1 kb in the fhaB gene and the chromosomal insertion at this locus of the gene coding for the truncated Sm28GST.

Figure 6:
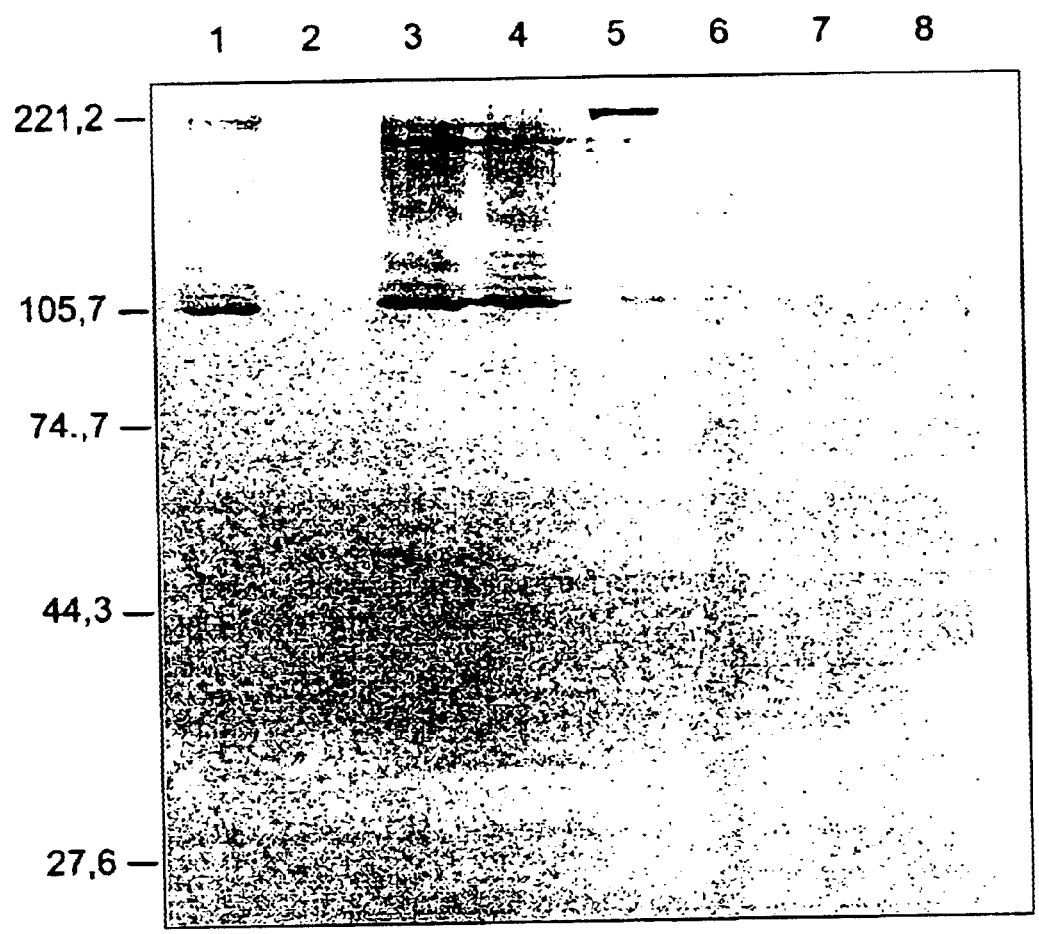
Figure 7:
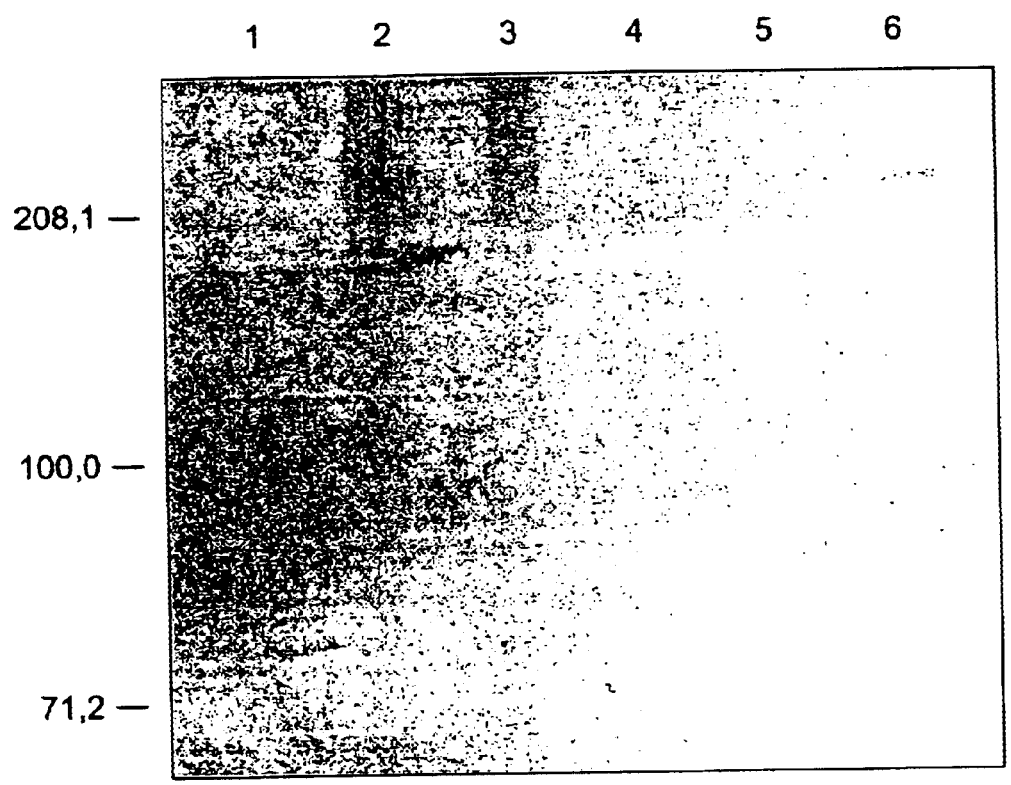

The fusion protein is detected in the protein fraction associated with the cells of the strain BPGR6 in which a protein band slightly larger than the FHA reacts both with anti-FHA antibodies (FIG. 6) and anti-Sm28GST antibodies (FIG. 7) but less than the strain BPGR5. On the other hand, when the supernatant of a stationary phase culture of the strain BPGR6 is concentrated on heparin-sepharose, a secretion product reacts with both the id anti-FHA and the anti-Sm28GST antibodies (FIGS. 7 and 8), thus demonstrating that the fusion protein is secreted by BPGR6 and/or exposed at the surface of the outside of the bacterium. The efficiency of the secretion of the complete fusion protein remains low since the secreted product is cleaved to a large extent, as already observed for the strain BPGR5.

IX. Construction of the *Bordetella pertussis* Strain BPGR60 Producing a Modified Sm28GST of *S. mansoni* fused to the FHA.

The Sm28GST contains a cysteine possibly capable of forming a disulfide bridge. Now the presence of disulfide bridges may be a limiting factor in the efficient export of proteins into the culture supernatant of Gram-negative bacteria (Klauser, T., Pohlner, J. and Meyer, T. F. (1990) EMBO J. 9, 1991–1999; Klauser, T., Pohlner, J. and Meyer, T. F. (1992) EMBO J. 11, 2327–2335). Hence we tried to produce a fusion protein between the FHA and a Sm28GST whose TGC codon coding for the cysteine (at position 140 in the protein) has been replaced by the AGC codon coding for a serine and in which the stop codon has been deleted. The resulting construction is hence such that the reading frame of fhaB is maintained after the insertion of the modified Sm28 gene.

The BglII-SalI fragment of the gene coding for the Sm28GST modified at the cysteine codon was amplified by PCR ("polymerase chain reaction") with the aid of specific primers complementary to these two regions of the gene. The sequences of the oligonucleotides used as primers of amplification are shown below: oligo 5': 5' TAAGGATC-CCCATGGCTGGCGAGCATATCAAG 3' (SEQ ID NO:5) and oligo 3': 5CCTGTCGACCCTTTCAGAGATTCGCT-GATCATATTGAG 3' (SEQ ID NO:6) The 0.44 kb product of the PCR was digested with PstI and SalI and the 0.28 kb fragment was cloned in the plasmid pUC7-28 digested beforehand with PstI-SalI which generates pUC7-28*. The plasmid pUC7-28 is a derivative of pUC7 digested with BamHI (removal of the internal PstI and SalI sites in pUC7) and ligated to the 0.64 kb BamHI fragment derived from the amplification by PCR of the entire cDNA coding for the Sm28GST. This amplification by PCR was performed with the following oligonucleotides: oligo 5': 5' TAAGGATC-CCCATGGCTGGCGAGCATATCAAG 3' (SEQ ID NO:7) oligo 3': 5' TAAGGATCCCGAAGGGAGTTGCAGGCCT-GTT 3' (SEQ ID NO:8) The sequences of the BamHI linkers were chosen so that these restriction sites are compatible on each side with the reading frame starting at the BglII site of the fhaB gene. The BamHI fragment of the plasmid pUC7-28* is thus isolated and cloned at the BglII site of the plasmid pRIT13202 which generates the plasmid pUC8-928*. This plasmid is then digested by EcoRI and the EcoRI fragment is introduced into the plasmid pGR5 previously digested with EcoRI. The resulting plasmid pGR540 is then introduced in the *E. coli* strain S17-1.

The *E. coli* strain S17-1(pGR540) is then crossed with *B. pertussis* BPGR4 in order to integrate the construction into the chromosomal fhaB locus as described in Example VII. After selection for the two recombination events and analysis by Southern blot, the *B. pertussis* strain BPGR60 is retained. This strain is thus a derivative of *B. pertussis* BPSM containing the chromosomal insertion of the gene coding for the modified Sm28GST at the BglII site of the fhab gene.

Figure 9:
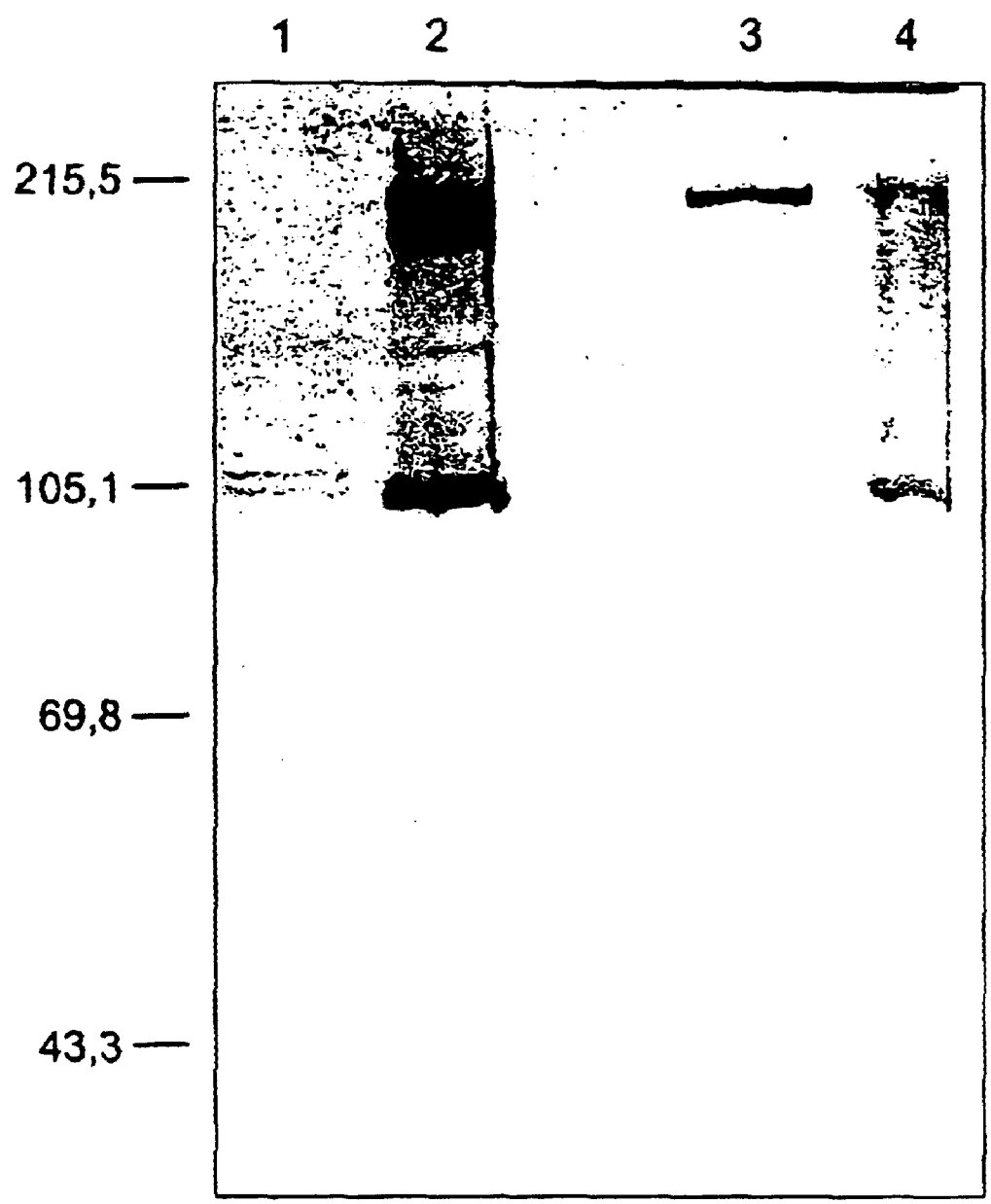
Figure 10:
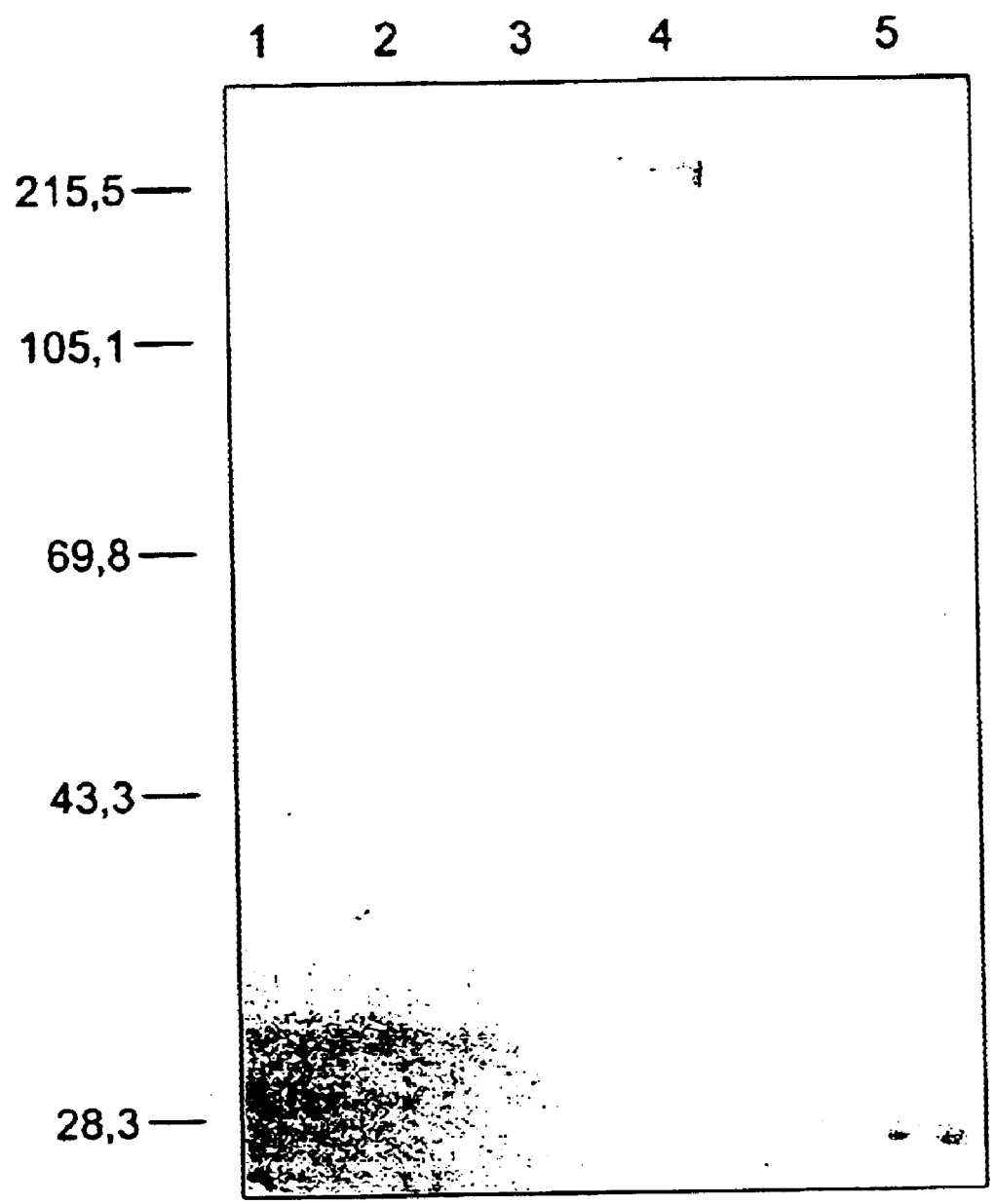

In the *B pertussis* strain BPGR60, the fusion protein is clearly visualized in the protein fraction associated with the cells in which a protein band reacts with both anti-FHA antibodies (FIG. 9) and anti-Sm28GST antibodies (FIG. 10). In the crude supernatant polypeptides reacting only with the anti-FHA antibodies are observed (FIG. 9). When the supernatant of a stationary phase culture of this stain BPGR60 is concentrated on heparin-sepharose, a secretion product revealed by both the anti-FHA and anti-Sm28GST antibodies is detected. This recognition is very similar to that of the strain BPGR6. The fusion protein is thus secreted and/or exposed at the outside surface of the bacterium. However, the efficiency of the secretion of the complete fusion protein remains low and here, too, the secreted product is cleaved to a large extent.

X. Study of the Colorization of Recombinant *B. pertussis* Strain BPGR60 in the Mouse after Administration by the Nasal Route.

In order to study the colonization of the recombinant son BPGR60 in the OF1 mouse (impure stain, female mice aged 4 weeks), 5×106 in bacteria in suspension in PBS (cells scraped from a culture on solid medium Bordet Gengou with defibrinated sheeps' blood (BG): Bordet, J. and Gengou, 0. (1906) Ann. Inst.Pasteur (Paris) 20, 731–741) were instilled into the nose in a volume of 25 μl per nostril under pentobarbital anesthesia. The lungs of 4 to 7 mice were excised 3 hours after instillation then at 7, 14, 21 and 28 days after instillation. The lungs were homogenized in 5 ml PBS, then the bacteria were counted after spreading of the homogenate on the BG solid medium containing 100 μg/ml streptomycin and 25 μg/ml nalidixic acid ($BGS_{100}N_{25}$).

As show in FIG. 11A (full circles), a colonization of the lungs is observed up to day 7, which is then followed by a fall until day 28 when practically all of the bacteria have been eliminated. The kinetics of colonization of BPGR60 is similar to that observed with the wild-type strain BPSM (open squares) except that in this experiment this latter was not completely eliminated 28 days after instillation.

In the case in which the mice first received the strain BPGR60 and then were given the virulent strain BPSM, the wild-type strain no longer exhibits a growth phase and its elimination is then accelerated (full triangles).

The colonization of the strain BPGR60 was also studied in the mouse infected beforehand with the wild-type strain Tohama I. Thus, 28 days after the instillation of Tohama 1, the mice received a dose of BPGR60 and the number of bacteria contained in their lungs was evaluated. In this case no growth phase of the BPGR60 strain is observed during the 7 days following the administration (FIG. 11B, full triangles). On the other hand, the fall in the number of bacteria with time was more rapid than that observed 7 days after the administration of BPGR60 in the naive mouse.

These results thus indicate that the recombinant strain behaves in vivo like the wild-type strain and that a prior infection by one of the two strains prevents the efficient colonization of the respiratory mucosa by the other strain.

XI. Study of the Production of Inflammatory Cytokines Subsequent to the Nasal Administration of the Recombinant *B. pertussis* Strain BPGR60 in the OF1 Mouse.

The presence of certain microorganisms or even microparticles can CD cause inflammatory reactions of the pulmonary mucosa related to the presence of cells capable of producing, after stimulation, factors such as the "tumor necrosis factor" (TNF-α) or interleukin-6 (Il-6). The two cytokines are usually produced locally and can be determined in the bronchoalveolar lavages. In some severe cases these factors may be detected in the serum.

As previously, $5\times10^6$ bacteria of the recombinant strain BPGR60 suspended in PBS (cells scraped from a culture on solid $BGS_{100}N_{25}$ medium) were instilled into the nose of the OF1 mouse in a volume of 25 μl per nostril under pentobarbital anesthesia. Mice receiving silica particles or PBS were used as controls. After 3, 6, 24 hours, then 3 and 7 days, bleeding and bronchoalveolar lavage were performed (5 mice per point).

Although no trace of TNF-α and Il-6 was detected in the circulating blood even after more than 7 days, significant quantities of the two cytokines were found in the bronchoalveolar lavages (FIG. 12).

The production of TNF seemed to be immediate since the maximal level of secretion was attained even at three hours after injection. Stable upto at least 6 hours after injection, the quantity of TNF-α was practically zero 24 hours after and remained negligible upto day 7.

The production of Il-6, very low the first three days, increased considerably on day 3, then returned to the normal level on day 7.

It seems thus that the administration of BPGR60 induces a localized inflammatory reaction, which is demonstrated by the increase of TNF and Il-6. This increase in the secretion of inflammatory cytokines was transient since normal levels of these cytokines were found in the lungs 7 days after instillation.

XII. Immune Response after Administration of the Recombinant *B. pertussis* Strain BPGR60 by the Nasal Route in the OF1 Mouse.

Four weeks old female OF1 mice received $5\times10^6$ bacteria in PBS suspension (cells scraped from a culture on solid $BGS_{100}N_{25}$ medium) in a volume of 25 μl per nostril under pentobarbital anesthesia. The immune response was evaluated in the blood and in the bronchoalveolar fluid 28, 35, 42, 49 and 56 days after administration. On day 56 some of these mice were then restimulated by a further injection of the strain BPGR60 (same conditions) or by 20 μg of purified recombinant antigen (Sm28GST produced in *E. coli*) by the nasal route. The immune response was then analyzed at days 70 and 77. This immune response was compared either to that of healthy mice raised under the same conditions or to that of mice having received only the recombinant antigen.

The results obtained in this example show us that only a serum response of the IgA type specific for the Sm28GST antigen is observed. This anti-Sm28GST response, which thus elicits no antibody of the IgG class, is observed 56 days after the first injection. The booster (D63) only induces the persistence of this specific IgA serum response. On the other hand, a strong anti-Fha response was detected. This response, observable from day 28 after administration, was maximal after 42 days and exhibited a plateau at the time of the booster. The booster by the scan BPGR60 (on D63) had no effect on this anti-Fha response, which had already attained its maximum.

The booster with the free protein Sm28GST by the nasal route causes a high production of IgG2a and IgG2b after 8 days. Fifteen days after this booster a strong anti-Sm28GST serum antibody response exhibiting the following isotypes IgG1, IgG2a,IgG2 b and IgA, is obtained.

The booster with the strain BPGR60 or the recombinant protein Sm28GST caused a slight increase in the quantity of anti-Fha secretory IgA 7 days after the second administration but the change was not significant. By day 77 (14 days after the booster) the anti-Fha level had fallen in the two groups.

On the other hand, the booster with BPGR60 induced an increase of the quantity of secretory antibodies specific for the Sm28GST 7 days afterwards which diminished 14 days afterwards. The booster with the recombinant protein caused a strong increase of the level of specific secretory IgA greater than that obtained with the sty BPGR60 but quite heterogeneous. This increase of anti-Sm28GST IgA did not last since from day 14 this level fell and returned to the values obtained just before the booster.

The study of antigen-antibody complexes of the IgA-Sm28GST type was conducted in the bronchoalveolar ravages before and after the booster with the stain BPGR60. The results obtained and presented in FIG. 14 show us that a large proportion of the anti-Sm28GST IgA exist in the form of complexes. This example shows us that the use of BPGR60 as booster formulation is perfectly suited to the production of a booster effect of the imune response towards the foreign antigen.

No production of anti-Sm28GST or anti-Fha IgA antibodies was detected in the bronchoalveolar secretions of mice having received only the Sm28GST as booster.

The administration by the nasal route of the strain BPGR60 expressing the Sm28GST is thus capable of inducing a secretory immune response towards this antigen. This antibody response may be amplified by the booster either with the recombinant strain or with the Sm28GST alone. This type of vaccination could doubtless be improved by delaying the time interval between the immunization and the booster (example: 90 days instead of 56). The quantities of bacteria and the dose of proteins may be considered to be optimal.

XIII. Study of the Protective Effect of the Immunization with BPGR60 on the Parasite Load of Mice Infected with *S. mansoni*

Prior to the infection, female OF1 mice were immunized according to the protocol indicated in the previous example and received a booster of the free protein (D63). Fifteen days after the booster, these mice were infested with 80 cercaria (transcutaneous route, abdomen). The parasite load was then evaluated 42 days after infestation by the verminous load and by the load of hepatic and intestinal eggs. The results obtained are compared to those obtained in the same experiment performed on untreated mice or mice having received only an injection of Sm28GST as booster.

Whereas the injection of Sm28GST alone does not cause significant effects on the parasitic load, the immunization with the aid of the stain BPGR60 induces a significant protection against the infection with *S. mansoni* whether assessed as verminous load (FIG. 15A) or number of eggs (FIG. 15B). This result indicates that a recombinant strain of *B. pertussis* expressing a foreign protein fused to the Fha possesses vaccinating properties.

XIV. Production and Secretion of the Truncated FHA in *Escherichia coli*

To permit the secretion of the truncated FHA in *E. coli*, the genes coding for the accessory protein FhaC and the protein FHA44 (coded initially by pBG4) were placed under the control of the tac promoter in order to take advantage of a regulable expression and to eliminate the regulatory system for the expression of FHA in *B. pertussis*. The 2.3. kb Bcl1 fragment of pRIT12990 (Delisse-Gathoye et al.,1990) containing the 3' end of the fimD gene and all of the fhaC gene was cloned in pQE32 (Qiagen, Hilden, Germany) previously digested with BamHI so as to generate a translational fusion between the sequence of the vector coding for a polyhistidine motif and the 3' end of fimD. As a result of this arrangement, the transcription of this hybrid gene and fhaC is under the control of the tac promoter inducible with IPTG. Moreover, the translation of the two genes, the 3' end of the first of which overlaps the 5' end of the second, may occur in a coupled manner. This plasmid is called pFJD6. A liquid culture of *E. coli* XLI blue transformed by this plasmid is treated with 1 mM IPTG for two hours after having attained an absorbance of. 0.8 at 600 nm. The cells were then harvested, lysed by sonication and the cell membranes are obtained by ultracentrifugation (15° C., 60 min 100,000×g) of the clarified sonicate. Extraction with sarkosyl (1%) selectively solubilizes the cytoplasmic membrane and a second ultracentrifugation (15° C., 60 min 100,000×g) leads to the isolation of a fraction enriched in proteins of the outer membrane. Their analysis by polyacrylamide gel electrophoresis in the presence of SDS and immunoblotting with a polyclonal serum directed against FhaC shows that a protein of the same size as FhaC of *B. pertussis* is present in these extracts whereas the untransformed strain does not possess it. These observations indicate that *E. coli* is capable of producing and correctly localizing FhaC in the cell.

The EcoRI-BamHI fragment coding for the truncated FHA (called FHA44) of pBG4 was cloned into the same sites of the vector pMMB91 (P. J. Fürste, W. Pansegrau, R. Frank, H. Blöcker, P. Scholz, M. Bagdasarian and E. Lanka, Gene 48, 119–131, 1986) under the control of the tac promoter. The resulting plasmid, pFJD9, was introduced by transformation into the *E. coli* strains XL1 blue and UT5600 (this latter does not produce the envelope protease OmpT), alone or in trans with pFJD6. The two plasmids possess compatible origins of replication and different resistance markers. An immunoblot performed on colonies possessing the two plasmids subcultured on solid medium containing 50 μM IPTG shows that the surface of the cells is recognized by an antiserum directed against the truncated FHA whereas no reactivity is detected at the surface of the cells possessing only one of the two plasmids. On the other hand, the fractionation of the cells and the analysis of the proteins by immunoblotting with the same antiserum does not lead to the detection of a protein band corresponding to FHA44, which suggests that the protein is produced at low levels or degraded to a large extent. In liquid culture detectable quantities of truncated FHA are not produced in the culture supernatant or in association with the cells either.

The extreme amino-terminal region of FHA hardly possesses the properties of a classical signal peptide and could hinder the efficient secretion of FHA in *E. coli*. Various constructions were made in order to add to them a pre-sequence coding for the signal peptide of the pre-protein preOmpA of *E. coli*. This pre-sequence was grafted on to three different sites of the 5' region of the truncated Fha gene. The 5' region of the gene was amplified by PCR starting from the plasmid pRIT13130 (Delisse-Gathoye et al., 1990) by using the oligonucleotide: 5'-3' TTTAACCGATGCGGCCGCCGTTG 3' (SEQ ID NO:9) which contains a Not1 site (underlined) and each of the three olidonucleotides (5'-3') TATAAGCTTCGAACCTGTACAGGCTGGTC (SEQ ID NO:10, TCAAAGCTTCGCGTGGTCAAGCGVGAAG and (SEQ ID NO:11) ATTAAGCTTCCCGGGCTTGGTTCCTCAG (SEQ ID NO:12), containing Hind3 sites (underlined). The 100 bp Xba1-BamHI fragment of pIN-OmpAIII-Hind (f. Rentier-Delrue, D. Swennen and J. Martial, Nucleic Acid Res. 16, 8726, 1988) containing the preOmpA pre-sequence was cloned in pACYC184 to give the plasmid pEC1. The three PCR products of 615 bp, 520 bp and 410 bp were then purified and digested by Not1 and Hind3 and each of them was used in a ligation to three partners with pEC1 restricted by Hind3 and BamHI and the 2 kb Not1-BamHI fragment of pRIT13197 coding for the 5' region of FHA44 (Delisse-Gathoye et al., 1990). The resulting three plasmids, pEC11, pEC12 and pEC13 were digested with Xba1, the site was filled in by the Klenow enzyme and the plasmids were redigested by BamHI. The DNA fragments containing the chimeric preOmpA-fha44 genes were cloned into the EcoRI sites (filled in with Klenow) and BamHI of pMMB91. The resulting plasmids, pFJD11, pFJD12 and pFJD13, encode chimeric genes whose products are fusion proteins in which the first 2, 33 and 71 amino acids, respectively, of FHA are replaced by the 18 amino acids of the signal peptide of preOmpA. The plasmids were introduced into the strain UT5600 alone or in trans with pFJD6 and the expression of fhaC and chimeric genes were induced by the addition of IPTG to the liquid cultures when they had reached an absorbance of 1 at 600 nm. The cultures were incubated for three hours in the presence of IPTG (1 mM final). FHA44 is detected by immunoblotting after polyacrylamide gel electrophoresis in the presence of SDS in the culture supernatants derived from the strains expressing FhaC. The production of FHA44 is quite low in the strains UT5600 (pFJD6, pFJD11) and UT5600 (pFJD13, pFJD6) but markedly higher in the strain UT5600 (pFJD12, pFJD6) which contains the chimeric gene of intermediate length. The production of FHA44 in the supernatant of this strain is estimated by ELISA and immunoblotting to be about 20% of the production of the truncated FHA in *B. pertussis* (BPGR44). On the other hand, the other two strains secrete 8 to 10 fold less of FHA44 than the strain UT5600 (PFJD 12, pFJD6). In the absence of FhaC, the secretion is negligible for UT5600 (pFJD1) and UT5600 (pFJD13) and very low for UT5600 (pFJD12), which indicates that the truncated FHA is secreted in *E. coli* by its accessory protein and is not released non-specifically. FHA44 secreted by *E. coli* has the same size as that of *B. pertussis* and it can be purified under the same conditions by affinity chromatography on heparin-sepharose. The sequencing of the amino-terminal domain of the two proteins shows that they undergo the same amino-terminal maturation.

This example shows that it is possible to cause the truncated FHA indistinguishable from that produced by *B. pertussis* to be secreted efficiently in other Gram-negative micro-organisms, pathogenic or non-pathogenic, with the transfer of the secretion apparatus—FhaC seems sufficient—and the remodelling of the amino-terminal region of the FHA. It is hence probable that it will possible to use similar constructions to express and secrete the complete or truncated FHA provided that the secretion sequences are functionally present this technology is also capable of being extended to other gram-negative bacteria, such as Salmonella, Vibrio and others.

What is claimed is:

1. A recombinant DNA encoding an; immunogenic fusion protein, wherein said recombinant DNA comprises a sequence (1) coding for a polypeptide heterologous with respect to a filamentous hemagglutinin of *Bordetella* (Fha) fused in the same reading frame with a sequence (2) placed upstream from said sequence (1), said sequence (2) coding for at least a part of the precursor of the Fha, this part comprising the site of interaction of the Fha with heparin, said sequence (2) being placed under the control of a promoter recognized by the polymerases of a cell transformed with said recombinant DNA and when introduced into a cell culture is expressed in said cell culture or exposed at the surface of cells, wherein said recombinant DNA is expressed as an immunogenic translational fusion protein.

2. The recombinant DNA according to claim 1, wherein the Pha is a Fha of *B. pertussis*.

3. The recombinant DNA according to claim 1, wherein the sequence (2) codes for a mature Fha protein.

4. The recombinant DNA according to claim 3, wherein the sequence (2) results from truncation of the sequence coding for the mature Fha protein on its C-terminal side.

5. The recombinant DNA according to claim 1, further comprising a sequence (3) upstream from the sequence (1), this sequence (3) consisting essentially of a truncated part of the mature protein, supplemented by the signal sequence of the precursor.

6. The recombinant DNA according to claim 1, wherein the sequence (2) comprises excretion signals of the sequence coding for the Fha and an N-terminal domain of Fha homologous to the N-terminal domains of the hemolysins ShlA and HpmA of *Serratis marcescens* and *Proteus mirabilis*.

7. The recombinant DNA according to claim 4, wherein the extension of the sequence (2) towards its C-terminus does not exceed the length that would no longer permit the direct excretion of the recombinant protein into the culture medium.

8. The recombinant DNA according to claim 1, wherein the polypeptide encoded in the sequence (2) contains at least a specific attachment site of the Fha to the mucosa.

9. The recombinant DNA according to claim 1, wherein the sequence (1) codes for a polypeptide having vaccinating properties against a given pathogenic agent.

10. The recombinant DNA according to claim 1, wherein said DNA further comprises a promoter recognized by the polymerases of a cell transformable with a vector containing the recombinant DNA and allowing the expression of the sequences (1) and (2) provided that an accessory gene of fhaC is also expressed in this cell.

11. The recombinant DNA according to claim 10, wherein the promoter is a promoter recognized by the polymerases of a bacterium of the *Bordetella* species, which in the natural product regulates the expression of the Fha protein.

12. A culture of prokaryotic cells transformed by a recombinant DNA according to claim 9, wherein the promoter of the recombinant DNA is recognized by the polymerases of sail; prokaryotic cells.

13. The culture according to claim 12, wherein the cells belong to a *Bordetella* species and carry a fhaC gene expressable in these cells.

14. The culture according to claim 12, wherein the recombinant DNA is incorporated in the chromosomal DNA of said cells.

15. The culture of cells according to claim 12, wherein the expression product of the sequence (1) is exposed at the cell surface.

16. The culture according to claim 12, wherein the sequence (2) contains at least one attachment site for the Fha to the mucosa or to eukaryotic cells, or to macrophages or epithelial cells.

17. The culture according to claim 16, wherein said culture is detoxified or attenuated.

18. An immunogenic composition directed against a defined pathogenic agent comprising as an active principle cells of the culture according to claim 14 in which the sequence (1) codes for an antigen characteristic of said pathogenic agent.

19. A process for the production of a recombinant heterologous protein containing a defined polypeptide sequence comprising transforming a culture of prokaryotic cells with a vector containing a recombinant DNA according to claim 1, said prokaryotic cells also containing a nucleotide sequence coding for FhaC which is expressed or also having been transferred, culturing said prokaryotic cells; and recovering the product excreted by the cells of this culture into their medium.

20. The process according to claim 19, wherein said prokaryotic cells are *Bordetella*.

21. The process according to claim 19, further comprising purifying the excretion product by placing the culture medium in contact with heparin immobilized on an insoluble support and recovering purified recombinant protein by dissociation of the complex which said recombinant protein formed with heparin.

22. A recombinant DNA encoding a recombinant immunogenic polypeptide, wherein said recombinant DNA comprises a sequence (1) coding for an antigenic polypeptide or peptide fused in the some reading frame with a sequence (2) placed upstream from said sequence (1), said sequence (2) coding for at least a N-terminal region of the precursor of the Fha which contains the site of interaction of the Fha with heparin, said sequence (2) allowing the recombinant polypeptide, when said recombinant DNA is expressed as a translational fusion protein in a *B. pertussis* cell culture, to be secreted into the culture medium or exposed at the cell surface.

23. A recombinant DNA comprising a sequence (1) coding for a polypeptide heterologous with respect to a filamentous hemagglutinin of *Bordetella* (Fha) fused in the sane reading frame with a sequence (2) placed upstream from said sequence (1), said sequence (2) coding for at least a part of the precursor of the Fha this part comprising at least the N-terminal region of a truncated mature Fha protein which contains the site of interaction of the Fha with heparin, said sequence (2), when placed under the control of a promoter recognized by the cellular polymerases of *B. pertussis* and introduced into a *B. pertussis* cell culture is expressed in this culture and excreted into the culture medium of these cells or exposed at the surface of these cells, wherein the resulting translational fusion protein facilitates the presentation of the antigen encoded by the heterologous sequence (1) to the mucosal immune system.

24. A vaccine composition for stimulating mucosal immunity comprising the cell culture according to claim 12.

25. A method for stimulating mucosal immunity, comprising administering nasally to a subject in need thereof a composition comprising the cell culture according to claim 12.

26. The recombinant DNA according to claim 22 or 23, wherein said sequence (1) codes for an antigenic polypeptide or peptide of a pathogenic agent.

27. A culture of bacterial cells belonging to a bacterial species other than *Bordetella* and transformed by a recombinant DNA encoding an immunogenic translational fusion protein comprising a sequence (1) coding for a polypeptide heterologous with respect to a filamentous hemagglutinin of *Bordetella* (Fha), said sequence (1) being fused in the same reading frame with a sequence (2) placed upstream from said sequence (1), said sequence (2) coding for at least a part of the precursor of the Fha, this part comprising the site of interaction of the Fha with heparin.

28. The cell culture according to claim 27, wherein the cells belong to the species *E. coli*.

29. The culture of bacterial cells according to claim 27 wherein said polypeptide heterologous with respect to a filamentous hemagglutinin of *Bordetella* (Fha) has vaccinating properties against a given pathogenic agent, and said part of the precursor of the Fha comprises at least the N-terminal region of a truncated mature Fha protein.

\* \* \* \* \*